(12) United States Patent
Greenberg et al.

(10) Patent No.: US 8,078,284 B2
(45) Date of Patent: Dec. 13, 2011

(54) RETINAL PROSTHESIS WITH A NEW CONFIGURATION

(75) Inventors: Robert J. Greenberg, Los Angeles, CA (US); Matthew J. McMahon, Los Angeles, CA (US); James Singleton Little, Saugus, CA (US); Kelly H. McClure, Simi Valley, CA (US); Brian V. Mech, Stevenson Ranch, CA (US); Neil Hamilton Talbot, Montrose, CA (US); Jordan M. Neysmith, Pasadena, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 1196 days.

(21) Appl. No.: 11/523,965

(22) Filed: Sep. 19, 2006

(65) Prior Publication Data

US 2007/0055336 A1    Mar. 8, 2007

Related U.S. Application Data

(63) Continuation-in-part of application No. 10/918,112, filed on Aug. 13, 2004, now Pat. No. 7,263,403.

(60) Provisional application No. 60/574,130, filed on May 25, 2004, provisional application No. 60/718,660, filed on Sep. 19, 2005, provisional application No. 60/718,769, filed on Sep. 19, 2005, now abandoned, provisional application No. 60/718,779, filed on Sep. 19, 2005.

(51) Int. Cl.
*A61N 1/00* (2006.01)
(52) U.S. Cl. ........................................................ 607/53
(58) Field of Classification Search ............... 607/53–54
See application file for complete search history.

(56) References Cited

U.S. PATENT DOCUMENTS

| | | | | |
|---|---|---|---|---|
| 4,628,933 | A | * | 12/1986 | Michelson ...................... 607/53 |
| 4,924,589 | A | * | 5/1990 | Leedy ................................ 438/6 |
| 5,109,844 | A | | 5/1992 | de Juan, Jr. et al. |
| 5,597,381 | A | * | 1/1997 | Rizzo, III ..................... 623/6.63 |
| 5,935,155 | A | | 8/1999 | Humayun et al. |

(Continued)

FOREIGN PATENT DOCUMENTS

WO    WO 03/043529 A2    5/2003

(Continued)

*Primary Examiner* — Mark W Bockelman
(74) *Attorney, Agent, or Firm* — Scott B. Dunbar; Alessandro Steinfl

(57) ABSTRACT

Polymer materials are useful as electrode array bodies for neural stimulation. They are particularly useful for retinal stimulation to create artificial vision, cochlear stimulation to create artificial hearing, and cortical stimulation, and many related purposes. The pressure applied against the retina, or other neural tissue, by an electrode array is critical. Too little pressure causes increased electrical resistance, along with electric field dispersion. Too much pressure may block blood flow. Common flexible circuit fabrication techniques generally require that a flexible circuit electrode array be made flat. Since neural tissue is almost never flat, a flat array will necessarily apply uneven pressure. Further, the edges of a flexible circuit polymer array may be sharp and cut the delicate neural tissue. By applying the right amount of heat to a completed array, a curve can be induced. With a thermoplastic polymer it may be further advantageous to repeatedly heat the flexible circuit in multiple molds, each with a decreasing radius. Further, it is advantageous to add material along the edges. It is further advantageous to provide a fold or twist in the flexible circuit array. Additional material may be added inside and outside the fold to promote a good seal with tissue.

18 Claims, 29 Drawing Sheets

U.S. PATENT DOCUMENTS

| | | | |
|---|---|---|---|
| 6,393,327 B1 * | 5/2002 | Scribner | 607/54 |
| 6,400,989 B1 | 6/2002 | Eckmiller | |
| 6,458,157 B1 | 10/2002 | Suaning | |
| 6,564,079 B1 | 5/2003 | Cory et al. | |
| 7,006,873 B2 * | 2/2006 | Chow et al. | 607/54 |
| 7,146,221 B2 * | 12/2006 | Krulevitch et al. | 607/116 |
| 2002/0111658 A1 | 8/2002 | Greenberg et al. | |
| 2003/0233134 A1 | 12/2003 | Greenberg et al. | |
| 2004/0094835 A1 | 5/2004 | Maghribi et al. | |

FOREIGN PATENT DOCUMENTS

| | | | |
|---|---|---|---|
| WO | WO 2004/011083 A1 | 2/2004 | |

* cited by examiner

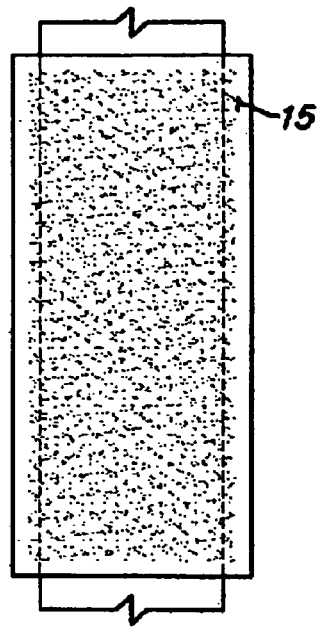
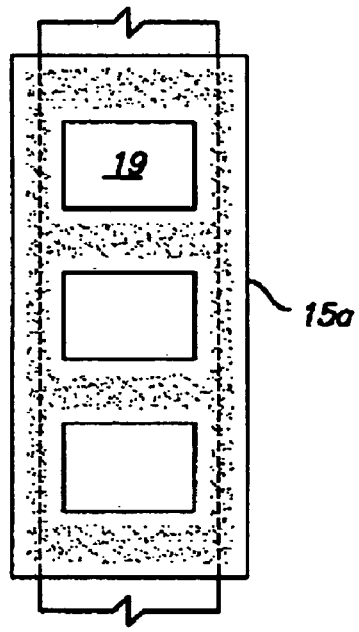
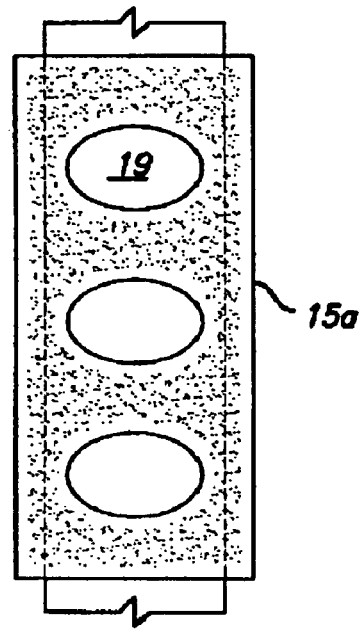
FIG. 31  FIG. 32  FIG. 33
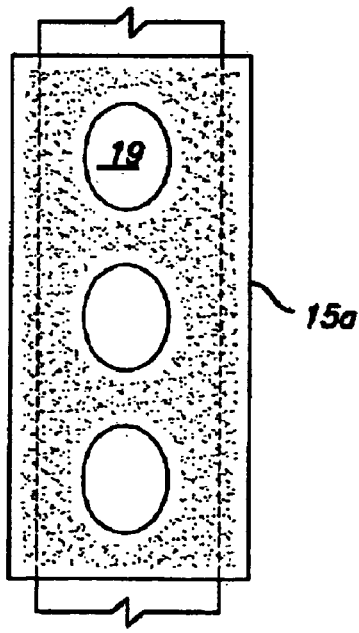
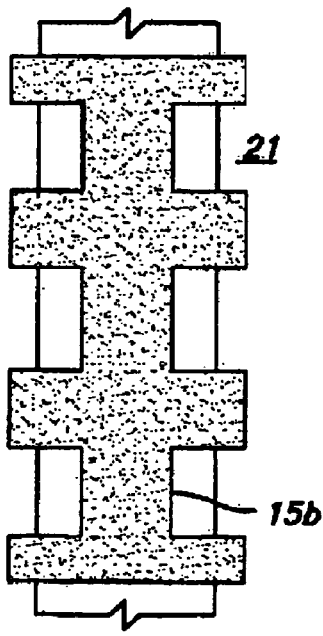
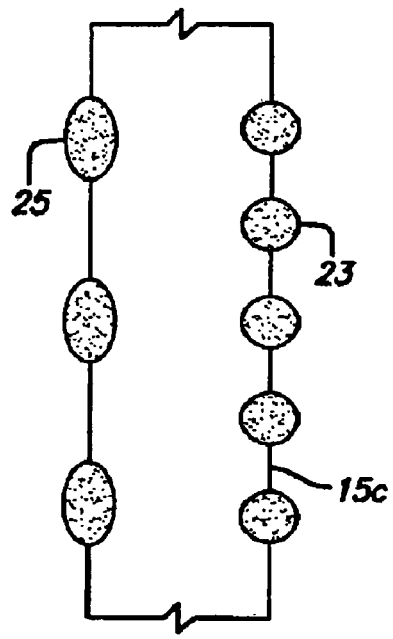
FIG. 34  FIG. 35  FIG. 36

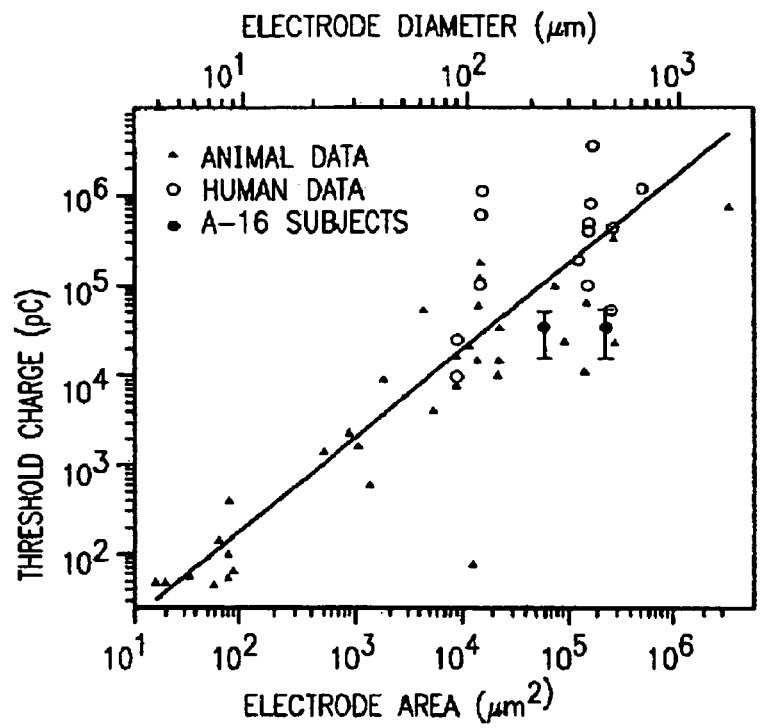
FIG. 56
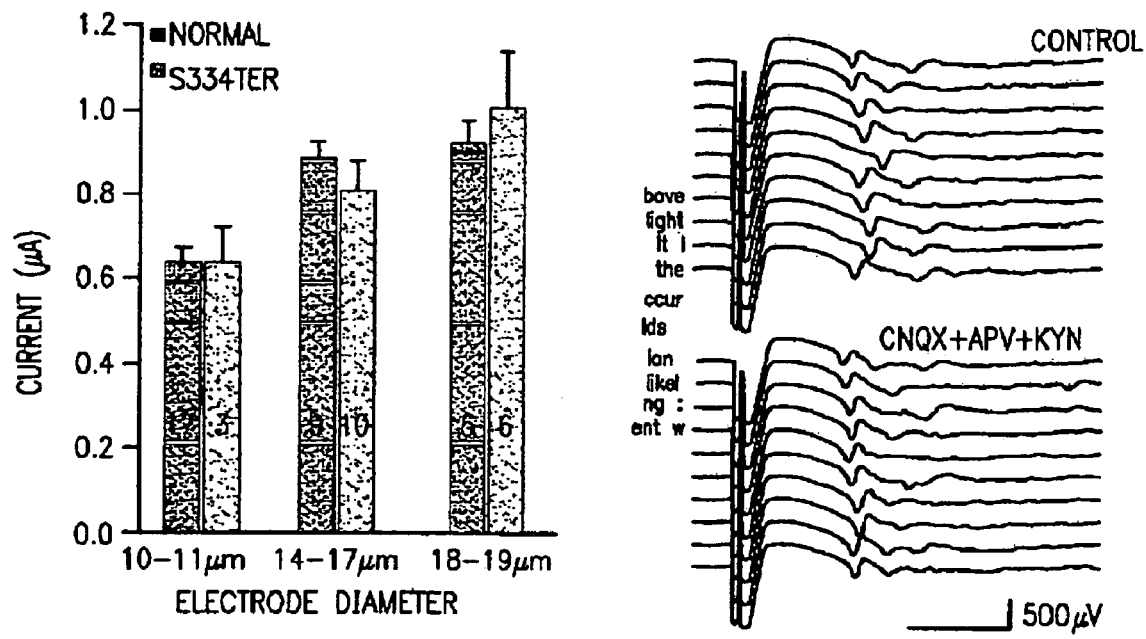
FIG. 57
FIG. 58

250 μV
5 ms

RETINAL PROSTHESIS WITH A NEW CONFIGURATION

CROSS-REFERENCE TO RELATED APPLICATIONS

This application claims the benefit of U.S. Provisional Application No. 60/718,660, entitled "System Architecture and Stimulation Methods for a Retinal Prosthesis", filed Sep. 19, 2005, the disclosures of which is incorporated herein by reference.

This application claims the benefit of U.S. Provisional Application No. 60/718,769 now abandoned, entitled "System for Testing and Configuring a Retinal Prosthesis", filed Sep. 19, 2005, the disclosures of which is incorporated herein by reference.

This application claims the benefit of U.S. Provisional Application No. 60/718,779, "Transretinal Flexible Circuit Electrode Array", filed Sep. 19, 2005, the disclosures of all which is incorporated herein by reference.

This application claims the benefit of U.S. patent application Ser. No. 11/521,281, "Transretinal Flexible Circuit Electrode Array", filed Sep. 13, 2006, the disclosures of which is incorporated herein by reference.

This application claims the benefit of U.S. patent application Ser. No. 11/413,689, "Flexible circuit electrode array", filed Apr. 28, 2006, which is a Continuation-In-Part of U.S. application Ser. No. 11/207,644, "Flexible circuit electrode array", filed Aug. 19, 2005 which claims the benefit of U.S. Provisional Application No. 60/676,008 "Thin Film Electrode Array", filed Apr. 28, 2005, the disclosures of all are incorporated herein by reference.

This application is a Continuation-in-Part of the U.S. patent application Ser. No. 10/918,112 "Retinal prosthesis", filed Aug. 13, 2004 now U.S. Pat. No. 7,263,403, which claims the benefit of U.S. Provisional Application No. 60/574,130 "Retinal Prosthesis", filed May 25, 2004, the disclosures of all are incorporated herein by reference.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved electrode array for neural stimulation.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatus to aid the visually impaired. Specifically, great effort has been expended in the area of intraocular retinal prosthetic devices in an effort to restore vision in cases where blindness is caused by photoreceptor degenerative retinal diseases; such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

SUMMARY OF THE INVENTION

Polymer materials are useful as electrode array bodies for neural stimulation. They are particularly useful for retinal stimulation to create artificial vision, cochlear stimulation to create artificial hearing, or cortical stimulation for many purposes. Regardless of which polymer is used, the basic construction method is the same. A layer of polymer is laid down, commonly by some form of chemical vapor deposition, spinning, meniscus coating or casting. A layer of metal, preferably platinum, is applied to the polymer and patterned to create electrodes and leads for those electrodes. Patterning is commonly done by photolithographic methods. A second layer of polymer is applied over the metal layer and patterned to leave openings for the electrodes, or openings are created later by means such as laser ablation. Hence the array and its supply cable are formed of a single body. Alternatively, multiple alternating layers of metal and polymer may be applied to obtain more metal traces within a given width.

The pressure applied against the retina, or other neural tissue, by an electrode array is critical. Too little pressure causes increased electrical resistance between the array and retina, along with electric field dispersion. Too much pressure may block blood flow causing retinal ischemia and hemorrhage. Pressure on the neural retina may also block axonal flow or cause neuronal atrophy leading to optic atrophy. Common flexible circuit fabrication techniques such as photolithography generally require that a flexible circuit electrode array be made flat. Since the retina is spherical, a flat array will necessarily apply more pressure near its edges, than at its center. Further, the edges of a flexible circuit polymer array may be quite sharp and cut the delicate retinal tissue. With most polymers, it is possible to curve them when heated in a mold. By applying the right amount of heat to a completed array, a curve can be induced that matches the curve of the retina. With a thermoplastic polymer such as liquid crystal polymer, it may be further advantageous to repeatedly heat the flexible circuit in multiple molds, each with a decreasing radius. Further, it is advantageous to add material along the edges of a flexible circuit array. Particularly, it is advantageous to add material that is more compliant than the polymer used for the flexible circuit array.

It is further advantageous to provide a fold or twist in the flexible circuit array at the point where it passes through the sclera. Additional material may be added inside and outside the fold to promote a good seal with the scleral tissue.

The novel features of the invention are set forth with particularity in the appended claims. The invention will be best understood from the following description when read in conjunction with the accompanying drawings.

BRIEF DESCRIPTION OF THE DRAWINGS

FIGS. 31-36 show several surfaces to be applied on top of the cable.

FIG. 56 shows a review of epiretinal stimulation thresholds.

FIG. 57 shows an electrode diameter.

FIG. 58 shows a respond to 10 stimulus pulses.

DETAILED DESCRIPTION OF THE PREFERRED EMBODIMENTS

The following description is of the best mode presently contemplated for practicing the invention. This description is not to be taken in a limiting sense, but is made merely for the purpose of describing the general principles of the invention. The scope of the invention should be determined with reference to the claims.

Figure 1:
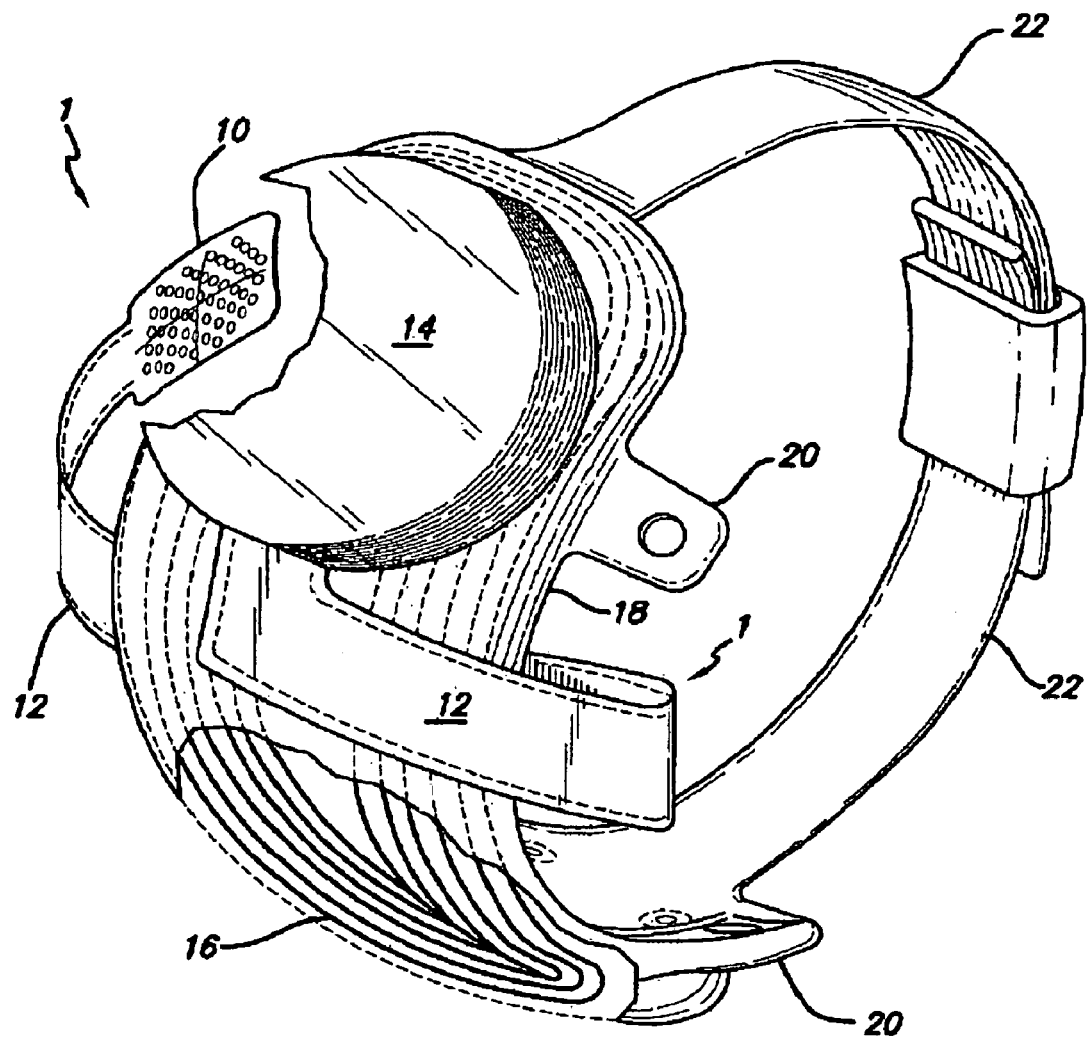
FIG. 1 is a perspective view of the implanted portion of the preferred retinal prosthesis.

FIG. 1 shows a perspective view of the implanted portion of the preferred retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by a molded body 18. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil.

It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

Figure 2:
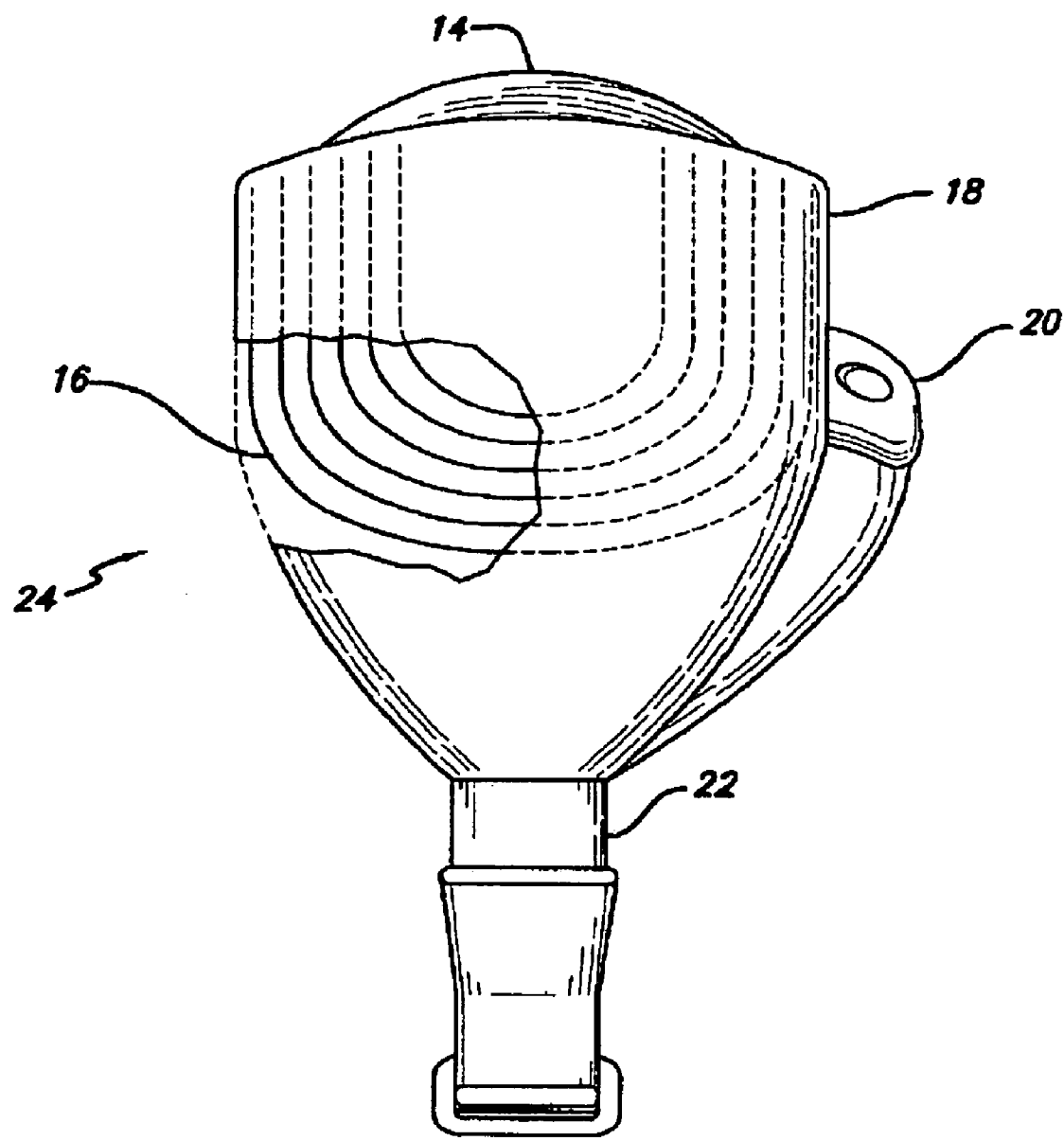
FIG. 2 is a side view of the implanted portion of the preferred retinal prosthesis showing the fan tail in more detail.
Figure 3A:
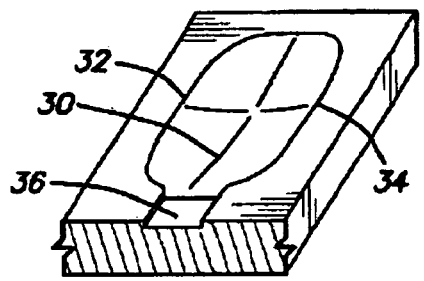
FIG. 3A-3E depict molds for forming the flexible circuit array in a curve.
Figure 3B:
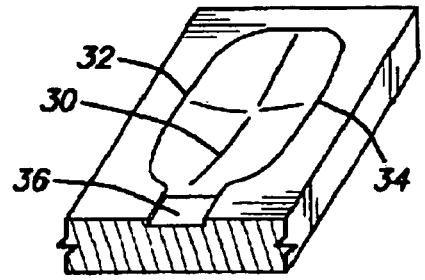
Figure 3C:
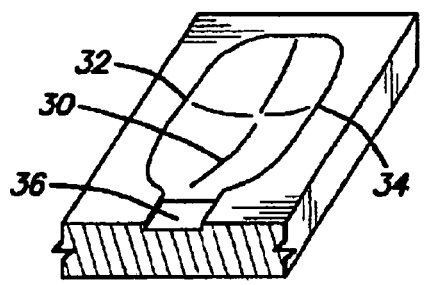
Figure 3D:
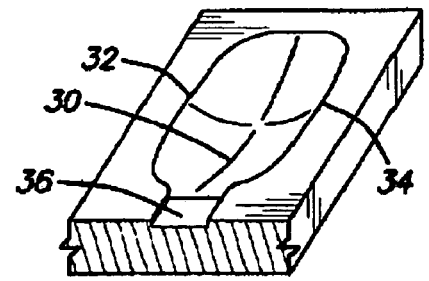
Figure 3E:
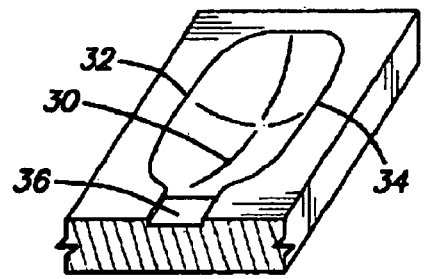

FIG. 2 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14.

The flexible circuit 1 is a made by the following process. First, a layer of polymer (such as polyimide, fluoro-polymers, silicone or other polymers) is applied to a support substrate (not part of the array) such as glass. Layers may be applied by spinning, meniscus coating, casting, sputtering or other physical or chemical vapor deposition, or similar process. Subsequently, a metal layer is applied to the polymer. The metal is patterned by photolithographic process. Preferably, a photo-resist is applied and patterned by photolithography followed by a wet etch of the unprotected metal. Alternatively, the metal can be patterned by lift-off technique, laser ablation or direct write techniques.

It is advantageous to make this metal thicker at the electrode and bond pad to improve electrical continuity. This can be accomplished through any of the above methods or electroplating. Then, the top layer of polymer is applied over the metal. Openings in the top layer for electrical contact to the electronics package 14 and the electrodes may be accomplished by laser ablation or reactive ion etching (RIE) or photolithograph and wet etch. Making the electrode openings in the top layer smaller than the electrodes promotes adhesion by avoiding delaminating around the electrode edges.

The pressure applied against the retina by the flexible circuit electrode array is critical. Too little pressure causes increased electrical resistance between the array and retina. It should be noted that while the present invention is described in terms of application to the retina, the techniques described are equally applicable to many forms of neural stimulation. Application to the retina requires a convex spherical curve. Application to the cochlea requires a constant curve in one dimension and a spiral curve in the other. Application to the cerebral cortex requires a concave spherical curve. Cortical stimulation is useful for artificial vision or hearing, touch and motor control for limb prostheses, deep brain stimulation for Parkinson's disease and multiple sclerosis, and many other applications.

Common flexible circuit fabrication techniques such as photolithography generally require that a flexible circuit electrode array be made flat. Since the retina is spherical, a flat array will necessarily apply more pressure near its edges, than at its center. With most polymers, it is possible to curve them when heated in a mold. By applying the right amount of heat to a completed array, a curve can be induced that matches the curve of the retina. To minimize warping, it is often advantageous to repeatedly heat the flexible circuit in multiple molds, each with a decreasing radius. FIG. 3 illustrates a series of molds according to the preferred embodiment. Since the flexible circuit will maintain a constant length, the curvature must be slowly increased along that length. As the curvature 30 decreases in successive molds (FIGS. 3A-3E) the straight line length between ends 32 and 34, must decrease to keep the length along the curvature 30 constant, where mold 3E approximates the curvature of the retina or other desired neural tissue. The molds provide a further opening 36 for the flexible circuit cable 12 of the array to exit the mold without excessive curvature.

It should be noted that suitable polymers include thermoplastic materials and thermoset materials. While a thermoplastic material will provide some stretch when heated a thermoset material will not. The successive molds are, therefore, advantageous only with a thermoplastic material. A thermoset material works as well in a single mold as it will with successive smaller molds. It should be noted that, particularly with a thermoset material, excessive curvature in three dimensions will cause the polymer material to wrinkle at the edges. This can cause damage to both the array and the retina. Hence, the amount of curvature is a compromise between the desired curvature, array surface area, and the properties of the material.

Figure 4:
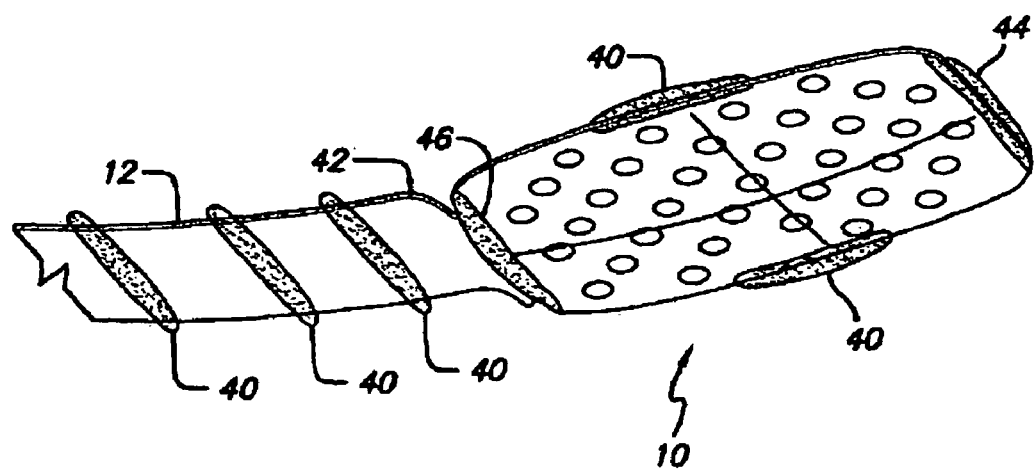
FIG. 4 depicts an alternate view of the invention with ribs to help maintain curvature and prevent retinal damage.

Referring to FIG. 4, the edges of the polymer layers are often sharp. There is a risk that the sharp edges of a flexible circuit will cut into delicate retinal tissue. It is advantageous to add a soft material, such as silicone, to the edges of a flexible circuit electrode array to round the edges and protect the retina. Silicone around the entire edge may make the flexible circuit less flexible. So, it is advantageous to provide silicone bumpers or ribs to hold the edge of the flexible circuit electrode array away from the retinal tissue. Curvature 40 fits against the retina. The leading edge 44 is most likely to cause damage and is therefore fit with molded silicone bumper. Also, edge 46, where the array lifts off the retina can cause damage and should be fit with a bumper. Any space along the side edges of curvature 40 may cause damage and may be fit with bumpers as well. It is also possible for the flexible circuit cable 12 of the electrode array to contact the retina. It is, therefore, advantageous to add periodic bumpers along the flexible circuit cable 12.

It is also advantageous to create a reverse curve or service loop in the flexible circuit cable 12 of the flexible circuit electrode array to gently lift the flexible circuit cable 12 off the retina and curve it away from the retina, before it pierces the sclera at a sclerotomy. It is not necessary to heat curve the service loop as described above, the flexible circuit electrode array can simply be bent or creased upon implantation. This service loop reduces the likelihood of any stress exerted extraocularly from being transmitted to the electrode region and retina. It also provides for accommodation of a range of eye sizes.

With existing technology, it is necessary to place the implanted control electronics outside of the sclera, while a retinal flexible circuit electrode array must be inside the sclera in order to contact the retina. The sclera is cut through at the pars plana, forming a sclerotomy, and the flexible circuit passed through the sclerotomy. A flexible circuit is thin but wide. The more electrode wires, the wider the flexible circuit must be. It may be difficult to seal a sclerotomy over a flexible circuit wide enough to support enough wires for a high resolution array. A narrow sclerotomy is preferable.

Figure 5:
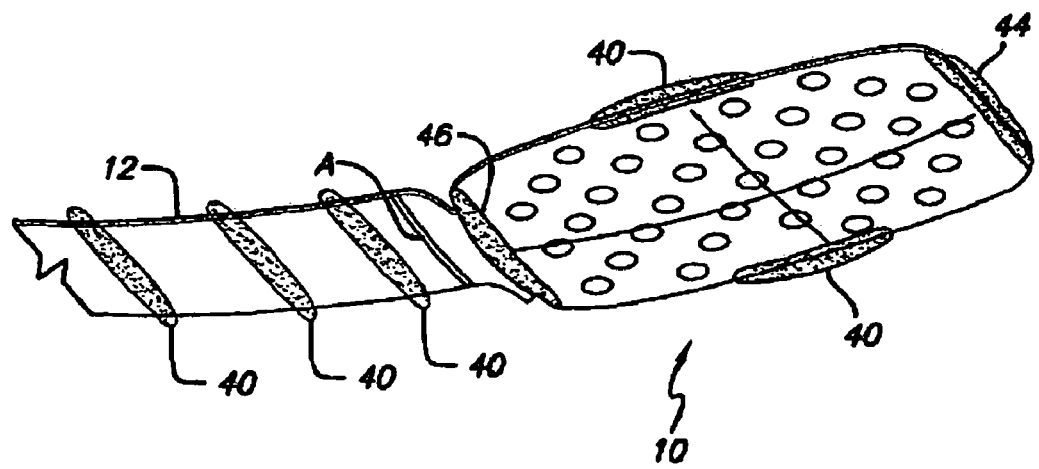
FIG. 5 depicts an alternate view of the invention with ribs to help maintain curvature and prevent retinal damage fold of the flexible circuit cable and a fold A between the circuit electrode array and the flexible circuit cable.

FIG. 5 depicts a further embodiment of the part of the prosthesis shown in FIG. 4 with a fold A between the circuit electrode array 10 and the flexible circuit cable 12. The angle in the fold A also called ankle has an angle of 1°-180°, preferably 80°-120°. The fold A is advantageous since it reduces tension and enables an effective attachment of the flexible electrode circuit array 10 to the retina.

Figure 6:
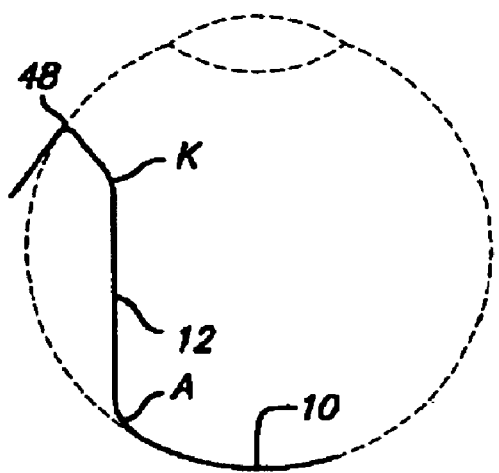
FIG. 6 depicts a cross-sectional view of the prosthesis shown inside of the eye with an angle in the fold of the flexible circuit cable and a fold between the circuit electrode array and the flexible circuit cable.

FIG. 6 depicts a side view of the prosthesis insight of the eye with an angle K of the flexible circuit cable 12 and a fold A between the circuit electrode array 10 and the flexible circuit cable 12. The angle K is about 45°-180° and preferably 80°-100°. The fold K also called knee is advantageous because it decreases pressure which would be applied by the flexible circuit cable 10.

Figure 7:
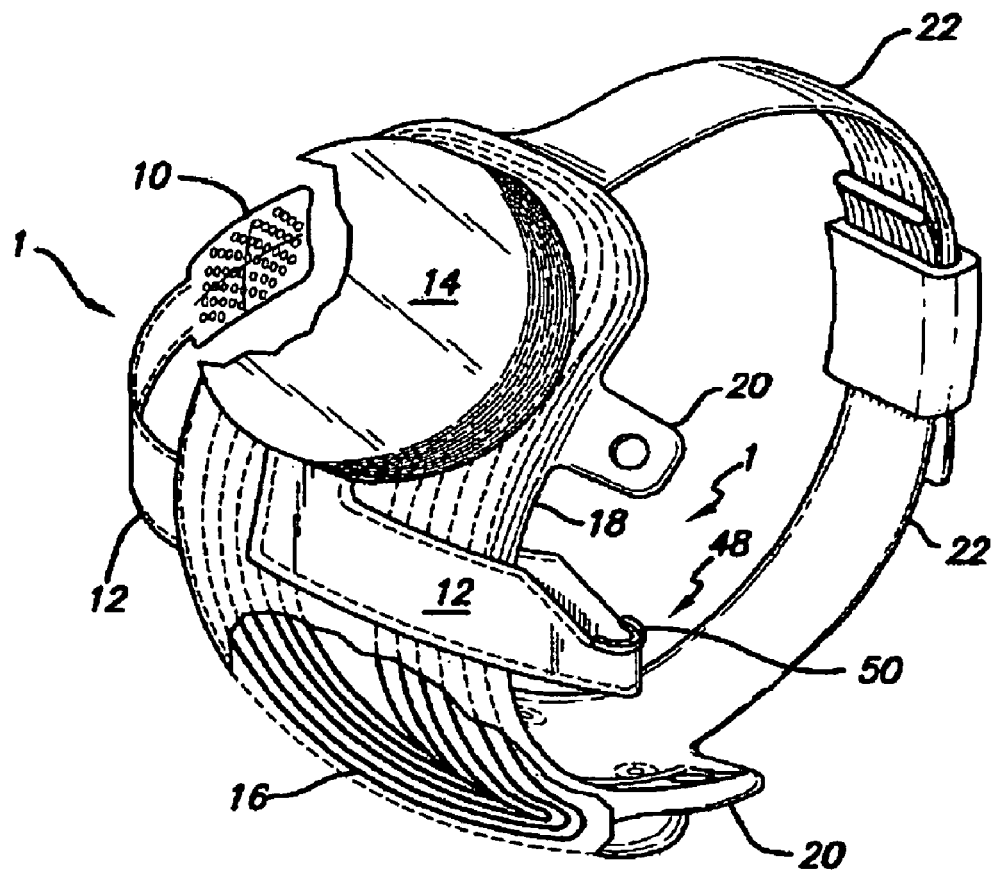
FIG. 7 depicts the implanted portion including a twist in the flexible circuit cable to reduce the width of a sclerotomy and a sleeve to promote sealing of the sclerotomy.

FIG. 7 shows the implanted portion of the retinal prosthesis including the additional feature of a gentle twist or fold 48 in the flexible circuit cable 12, where the flexible circuit cable 12 passes through the sclera (sclerotomy). The twist may be a simple sharp twist, or fold 48; or it may be a longer twist, forming a tube. While the tube is rounder, it reduces the flexibility of the flexible circuit. A simple fold 48 reduces the width of the flexible circuit with only minimal impact on flexibility.

Further, silicone or other pliable substance may be used to fill the center of the tube or fold 48 formed by the twisted flexible circuit cable 12. Further it is advantageous to provide a sleeve or coating 50 that promotes healing of the sclerotomy. Polymers such as polyimide, which may be used to form the flexible circuit cable 12 and flexible circuit electrode array 10, are generally very smooth and do not promote a good bond between the flexible circuit cable 12 and scleral tissue. A sleeve or coating of polyester, collagen, silicone, Gore-tex or similar material would bond with scleral tissue and promote healing. In particular, a porous material will allow scleral tissue to grow into the pores promoting a good bond.

Alternatively, the flexible circuit electrode array 10 may be inserted through the sclera, behind the retina and placed between the retina and choroid to stimulate the retina subretinally. In this case, it is advantageous to provide a widened portion, or stop, of the flexible circuit cable 12 to limit how far the flexible circuit electrode array is inserted and to limit the transmission of stress through the sclera. The stop may be widening of the flexible circuit 1 or it may be added material such as a bumper or sleeve.

Human vision provides a field of view that is wider than it is high. This is partially due to fact of having two eyes, but even a single eye provides a field of view that is approximately 90° high and 140° to 160° degrees wide. It is therefore, advantageous to provide a flexible circuit electrode array 10 that is wider than it is tall. This is equally applicable to a cortical visual array. In which case, the wider dimension is not horizontal on the visual cortex, but corresponds to horizontal in the visual scene.

Figure 8:
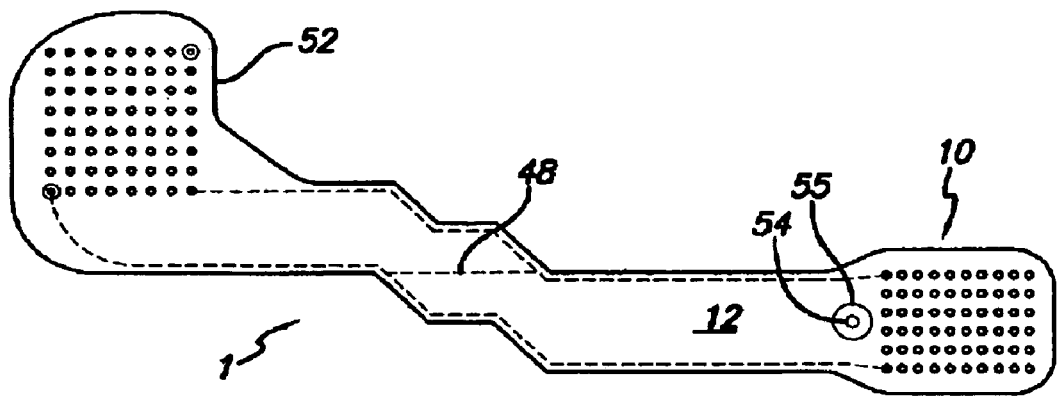
FIG. 8 depicts the flexible circuit array before it is folded and attached to the implanted portion.

FIG. 8 shows the flexible circuit electrode array prior to folding and attaching the array to the electronics package 14. At one end of the flexible circuit cable 12 is an interconnection pad 52 for connection to the electronics package 14. At the other end of the flexible circuit cable 12 is the flexible circuit electrode array 10. Further, an attachment point 54 is provided near the flexible circuit electrode array 10. A retina tack (not shown) is placed through the attachment point 54 to hold the flexible circuit electrode array 10 to the retina. A stress relief 55 is provided surrounding the attachment point 54. The stress relief 55 may be made of a softer polymer than the flexible circuit, or it may include cutouts or thinning of the polymer to reduce the stress transmitted from the retina tack to the flexible circuit electrode array 10. The flexible circuit cable 12 is formed in a dog leg pattern so than when it is folded at fold 48 it effectively forms a straight flexible circuit cable 12 with a narrower portion at the fold 48 for passing through the sclerotomy.

Figure 9:
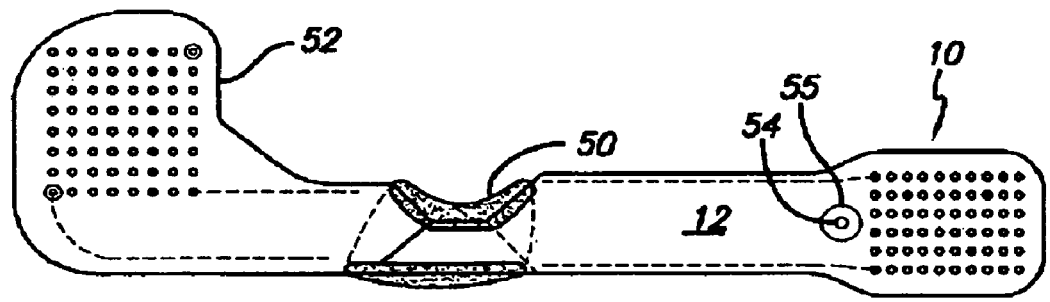
FIG. 9 depicts the flexible circuit array folded.

FIG. 9 shows the flexible circuit electrode array after the flexible circuit cable 12 is folded at the fold 48 to form a narrowed section. The flexible circuit cable 12 may include a twist or tube shape as well. With a retinal prosthesis as shown in FIG. 1, the bond pad 52 for connection to the electronics package 14 and the flexible circuit electrode array 10 are on opposite side of the flexible circuit. This requires patterning, in some manner, both the base polymer layer and the top polymer layer. By folding the flexible circuit cable 12 of the flexible circuit electrode array 10, the openings for the bond pad 52 and the electrodes are on the top polymer layer and only the top polymer layer needs to be patterned.

Also, since the narrowed portion of the flexible circuit cable 12 pierces the sclera, shoulders formed by opposite ends of the narrowed portion help prevent the flexible circuit cable 12 from moving through the sclera. It may be further advantageous to add ribs or bumps of silicone or similar material to the shoulders to further prevent the flexible circuit cable 12 from moving through the sclera.

Further it is advantageous to provide a suture tab 56 in the flexible circuit body near the electronics package to prevent any movement in the electronics package from being transmitted to the flexible circuit electrode array 10. Alternatively, a segment of the flexible circuit cable 12 can be reinforced to permit it to be secured directly with a suture.

An alternative to the bumpers described in FIG. 4, is a skirt of silicone or other pliable material as shown in FIGS. 10, 11, 12, and 13. A skirt 60 covers the flexible circuit electrode array 10, and extends beyond its edges. It is further advantageous to include wings 62 adjacent to the attachment point to spread any stress of attachment over a larger area of the retina. There are several ways of forming and bonding the skirt 60. The skirt 60 may be directly bonded through surface activation or indirectly bonded using an adhesive.

Alternatively, a flexible circuit electrode array 10 may be layered using different polymers for each layer. Using too soft of a polymer may allow too much stretch and break the metal traces. Too hard of a polymer may cause damage to delicate neural tissue. Hence a relatively hard polymer, such a polyimide may be used for the bottom layer and a relatively softer polymer such a silicone may be used for the top layer including an integral skirt to protect delicate neural tissue.

Figure 11:
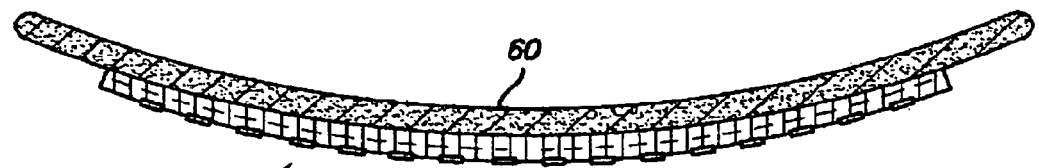
FIG. 11 depicts a flexible circuit array with a protective skirt bonded to the back side of the flexible circuit array.
Figure 12:
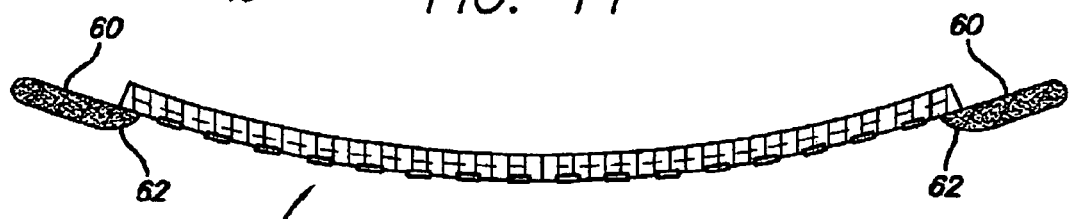
FIG. 12 depicts a flexible circuit array with a protective skirt bonded to the front side of the flexible circuit array.

The simplest solution is to bond the skirt 60 to the back side (away from the retina) of the flexible circuit electrode array 10 as shown in FIG. 11. While this is the simplest mechanical solution, sharp edges of the flexible circuit electrode array 10 may contact the delicate retina tissue. Bonding the skirt to the front side (toward the retina) of the flexible circuit electrode array 10, as shown in FIG. 12, will protect the retina from sharp edges of the flexible circuit electrode array 10. However, a window 62 must be cut in the skirt 60 around the electrodes. Further, it is more difficult to reliably bond the skirt 60 to the flexible circuit electrode array 10 with such a small contact area. This method also creates a space between the electrodes and the retina which will reduce efficiency and broaden the electrical field distribution of each electrode. Broadening the electric field distribution will limit the possible resolution of the flexible circuit electrode array 10.

Figure 13:
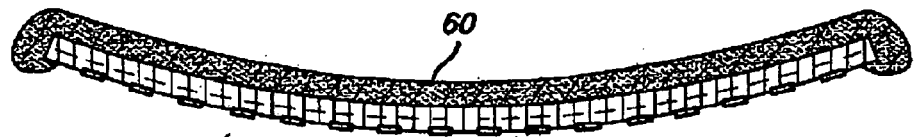
FIG. 13 depicts a flexible circuit array with a protective skirt bonded to the back side of the flexible circuit array and molded around the edges of the flexible circuit array.

FIG. 13 shows another structure where the skirt 60 is bonded to the back side of the flexible circuit electrode array 10, but curves around any sharp edges of the flexible circuit electrode array 10 to protect the retina. This gives a strong bond and protects the flexible circuit electrode array 10 edges. Because it is bonded to the back side and molded around the edges, rather than bonded to the front side, of the flexible circuit electrode array 10, the portion extending beyond the front side of the flexible circuit electrode array 10 can be much smaller. This limits any additional spacing between the electrodes and the retinal tissue.

Figure 14:
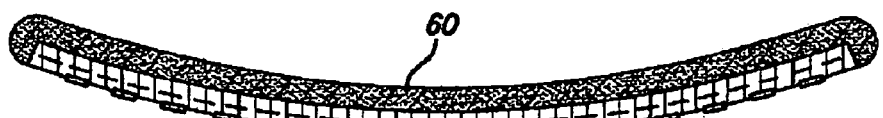
FIG. 14 depicts a flexible circuit array with a protective skirt bonded to the back side of the flexible circuit array and molded around the edges of the flexible circuit array and flush with the front side of the array.

FIG. 14 shows a flexible circuit electrode array 10 similar to FIG. 13, with the skirt 60, flush with the front side of the flexible circuit electrode array 10 rather than extending beyond the front side. While this is more difficult to manufacture, it does not lift the electrodes off the retinal surface as with the array in FIG. 10. It should be noted that FIGS. 11, 13, and 14 show skirt 60 material along the back of the flexible circuit electrode array 10 that is not necessary other than for bonding purposes. If there is sufficient bond with the flexible circuit electrode array 10, it may advantageous to thin or remove portions of the skirt 60 material for weight reduction.

Figure 10:
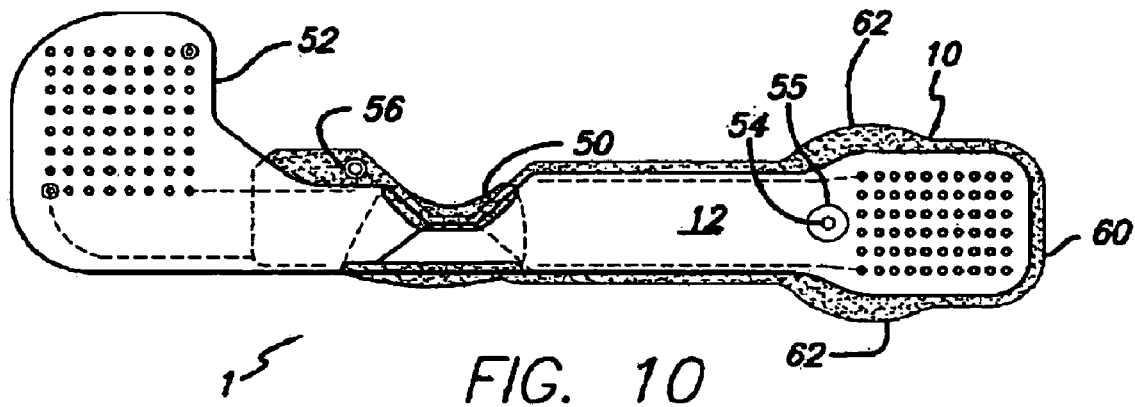
FIG. 10 depicts a flexible circuit array with a protective skirt.
Figure 15:
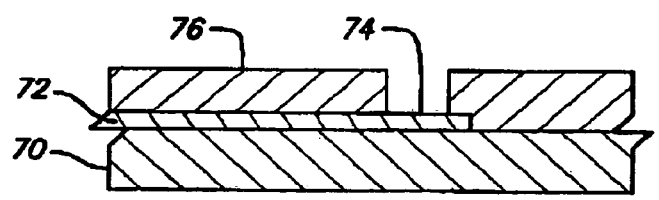
FIG. 15 is an enlarged view of a single electrode within the flexible circuit electrode array.

Referring to FIG. 15, the flexible circuit electrode array is manufactured in layers. A base layer of polymer 70 is laid down, commonly by some form of chemical vapor deposition, spinning, meniscus coating or casting. A layer of metal 72 (preferably platinum) is applied to the polymer base layer 70 and patterned to create electrodes 74 and traces for those electrodes. Patterning is commonly done by photolithographic methods. The electrodes 74 may be built up by electroplating or similar method to increase the surface area of the electrode 74 and to allow for some reduction in the electrodes 74 over time. Similar plating may also be applied to the bond pads 52 (FIGS. 8-10). A top polymer layer 76 is applied over the metal layer 72 and patterned to leave openings for the electrodes 74, or openings are created later by means such as laser ablation. It is advantageous to allow an overlap of the top polymer layer 76 over the electrodes 74 to promote better adhesion between the layers, and to avoid increased electrode reduction along their edges. The overlapping top layer promotes adhesion by forming a clamp to hold the metal electrode between the two polymer layers. Alternatively, multiple alternating layers of metal and polymer may be applied to obtain more metal traces within a given width.

Figure 16:
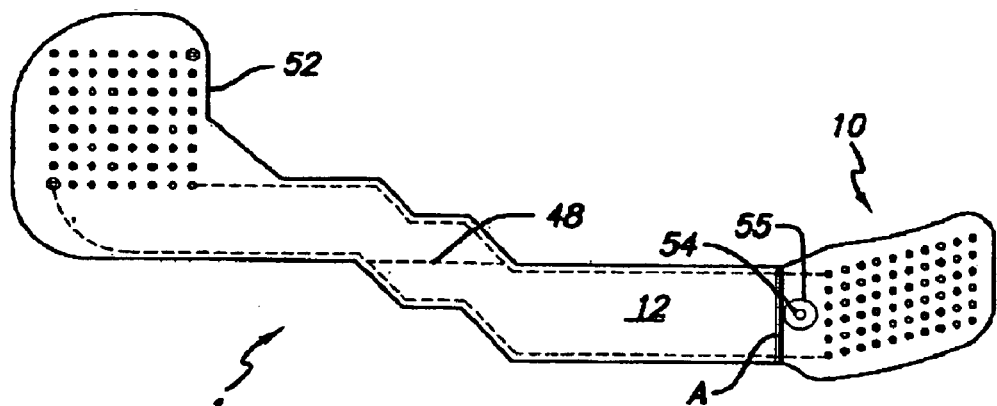
FIG. 16 depicts the flexible circuit array before it is folded and attached to the implanted portion containing an additional fold between the flexible electrode array and the flexible cable.

FIG. 16 depicts the flexible circuit array 1 before it is folded and attached to the implanted portion containing an additional fold A between the flexible electrode array 10 and the flexible cable 12. The angle in the fold A, also called ankle, has an angle of 1°-180°, preferably 80°-120°. The ankle is advantageous in the process of inserting the prostheses in the eye and attaching it to the retina.

Figure 17:
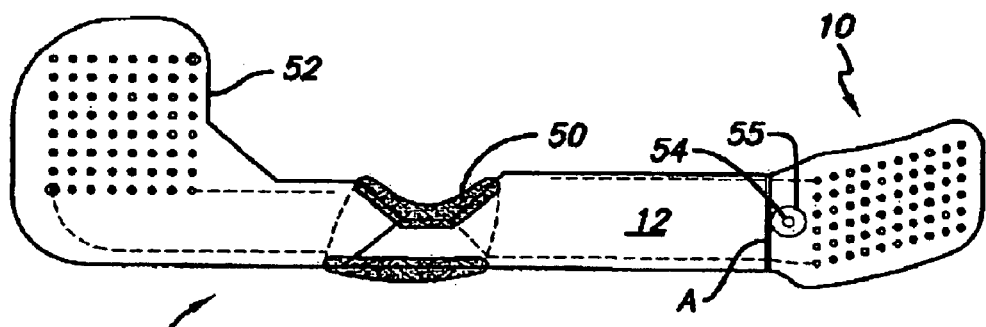
FIG. 17 depicts the flexible circuit array of FIG. 16 folded containing an additional fold between the flexible electrode array and the flexible cable.

FIG. 17 depicts the flexible circuit array 1 of FIG. 16 folded containing an additional fold A between the flexible electrode array 10 and the flexible cable 12. The flexible circuit array as shown in FIGS. 8 and 16 differ by the fold A from each other.

Figure 18:
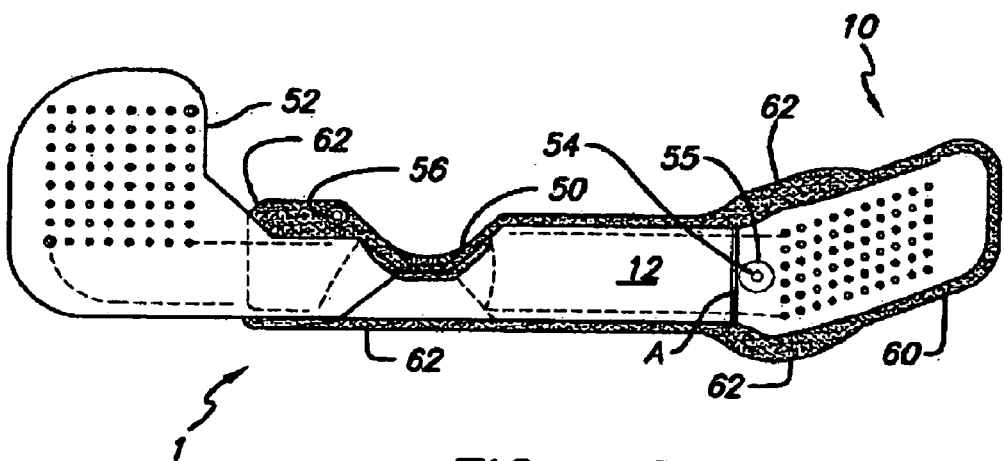
FIG. 18 depicts a flexible circuit array of FIG. 17 with a protective skirt and containing an additional fold between the flexible electrode array and the flexible cable.

FIG. 18 depicts a flexible circuit array of FIG. 17 with a protective skirt 60 and containing an additional fold A between the flexible electrode 10 array and the flexible cable 12. The flexible circuit array as shown in FIGS. 10 and 18 differ by the fold A from each other.

Figure 19:
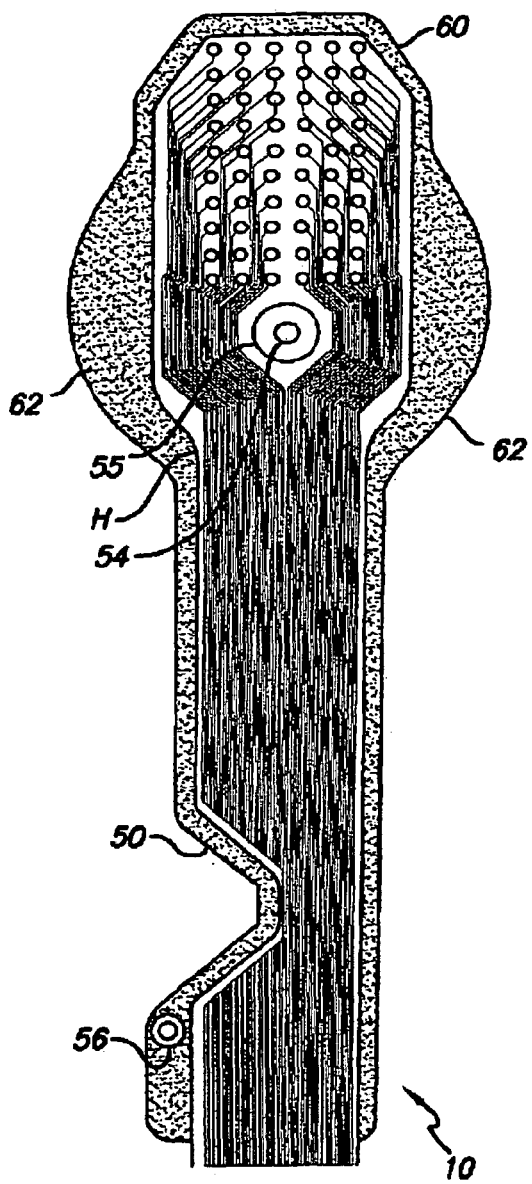
FIG. 19 depicts a top view of a flexible circuit array and flexible circuit cable showing an additional horizontal angel between the flexible electrode array and the flexible cable.

FIG. 19 depicts a top view of a flexible circuit array and flexible circuit cable showing the additional horizontal angel H between the flexible electrode array 10 and the flexible cable 12. The angle H is from about 1° to about 90° and preferably from about 30° to about 60°.

Figure 20:
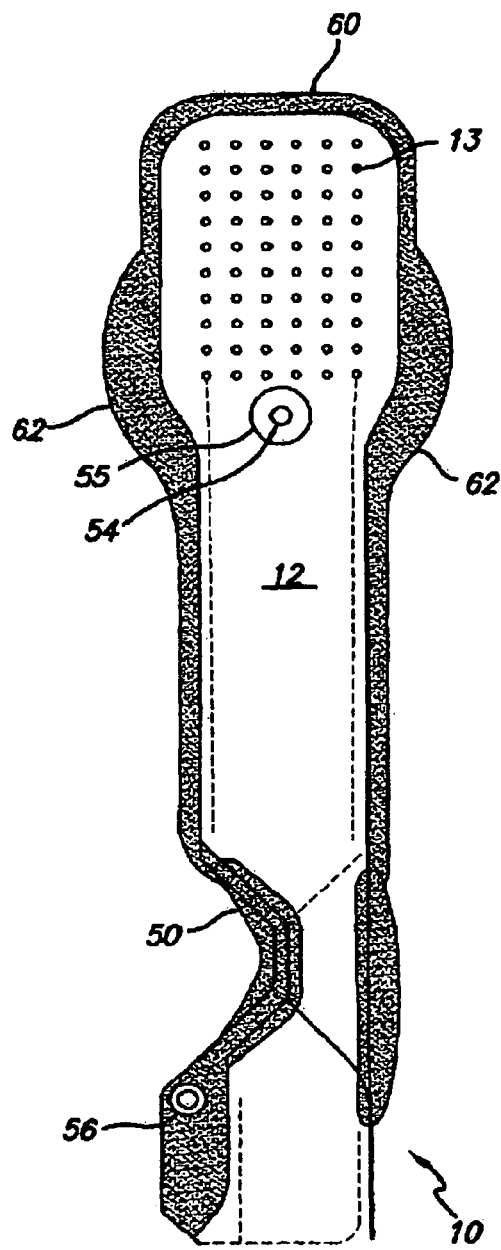
FIG. 20 depicts another variation without the horizontal angel between the flexible electrode array and the flexible cable but with an orientation of the electrodes in the flexible electrode array as shown for the variation in FIG. 19.

FIG. 20 depicts another variation without the horizontal angel H between the flexible electrode array 10 and the flexible cable 12 but with an orientation of the electrodes in the flexible electrode array 12 as shown in FIG. 19 for a flexible electrode array 10. The grid of electrodes 13 has the angle H with the flexible cable which can be the same as the angel H in the flexible electrode array 10 of FIG. 19.

Both variation shown in FIGS. 19 and 20 have the advantage that the electrodes are oriented horizontally if they are inserted into the eye. Further, both variations as shown in FIGS. 19 and 20 can also additionally contain a fold K (FIG. 6).

Figure 21:
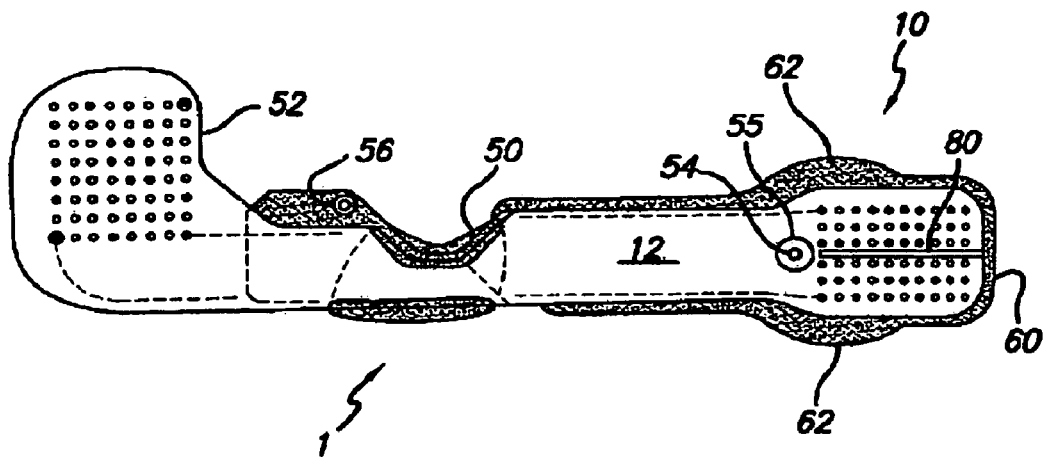
FIG. 21 depicts a top view of a flexible circuit array and flexible circuit cable wherein the array contains a slit along the length axis.

FIG. 21 depicts a top view of a flexible circuit array and flexible circuit cable as shown in FIGS. 10 and 18 wherein the array contains a slit along the length axis.

Figure 22:
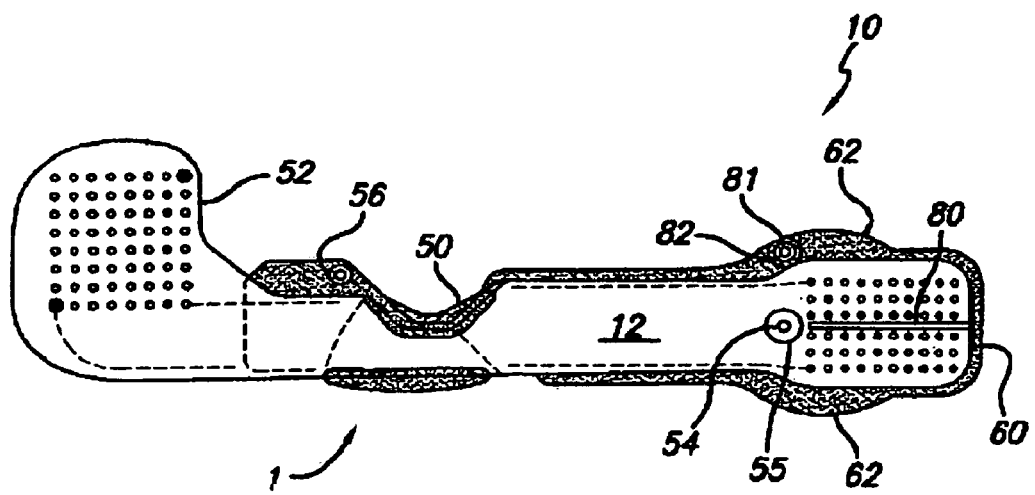
FIG. 22 depicts a top view of a flexible circuit array and flexible circuit cable wherein the array contains a slit along the length axis with two attachment points.

FIG. 22 depicts a skirt of silicone or other pliable material as shown in FIG. 10 to 14. A skirt 60 covers the flexible circuit electrode array 10, and extends beyond its edges. In this embodiment of the present invention the flexible circuit electrode array contains a slit 80 along the lengths axis. Further, according to this embodiment, the skirt of silicone or other pliable material contains preferably at least two attachment points 81 and stress reliefs 82 are provided surrounding the attachment points 81. The attachment points 81 are located preferably on the skirt 60 outside the flexible circuit electrode 10 and are positioned apart as far as possible from each other. The two tacks 81 are far enough apart not to cause tenting, therefore fibrosis between the two tacks which cause a traction detachment of the retina. Furthermore, the polyimide is completely between the two tacks, which also reduce the possibility of tenting. Also, this orientation of tacks keeps the tacks away from the axons, which arise from the ganglion cells which are intended to be activated. The wings 62 serve as external tabs or strain reliefs. The multiple tacks prevent rotation of the array.

The stress relief 82 may be made of a softer polymer than the flexible circuit, or it may include cutouts or thinning of the polymer to reduce the stress transmitted from the retina tack to the flexible circuit electrode array 10.

Figure 23:
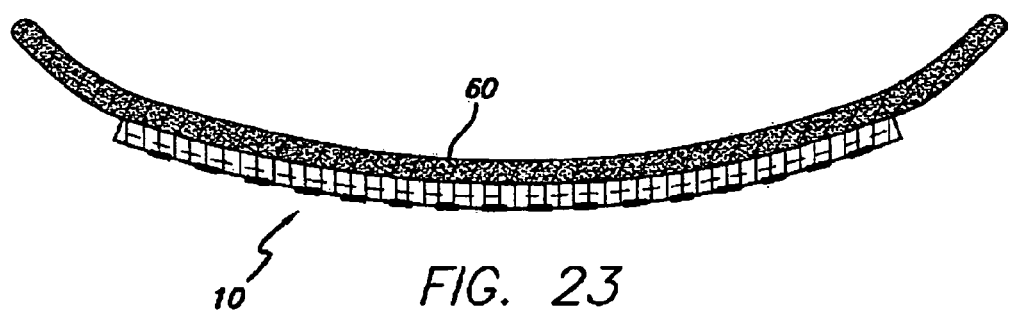
FIG. 23 depicts a flexible circuit array with a protective skirt bonded to the back side of the flexible circuit array with a progressively decreasing radius.

FIG. 23 depicts a flexible circuit array 10 with a protective skirt 60 bonded to the back side of the flexible circuit array 10 with a progressively decreasing radius.

Figure 24:
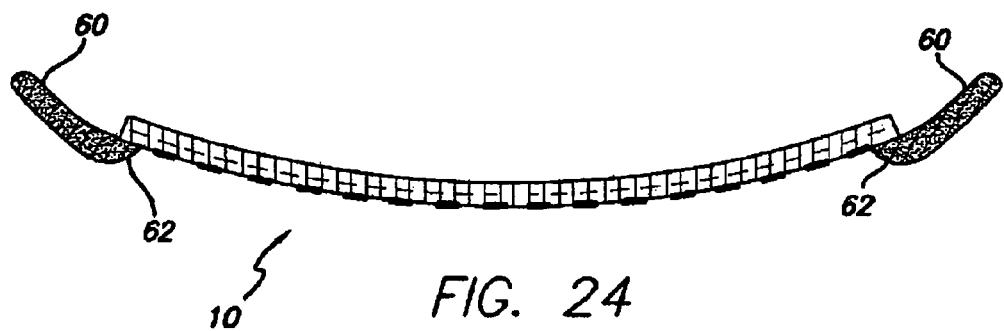
FIG. 24 depicts a flexible circuit array with a protective skirt bonded to the front side of the flexible circuit array with a progressively decreasing radius.

FIG. 24 depicts a flexible circuit array 10 with a protective skirt 60 bonded to the front side of the flexible circuit array 10 with a progressively decreasing radius.

Figure 25:
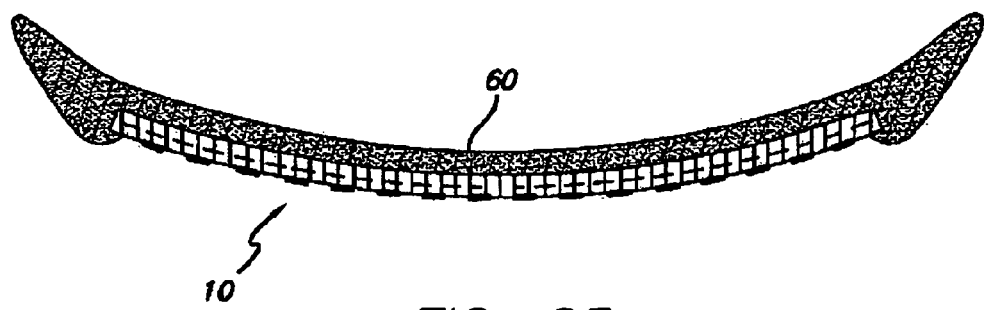
FIG. 25 depicts a flexible circuit array with a protective skirt bonded to the back side of the flexible circuit array and molded around the edges of the flexible circuit array with a progressively decreasing radius.

FIG. 25 depicts a flexible circuit array 10 with a protective skirt 60 bonded to the back side of the flexible circuit array 10 and molded around the edges of the flexible circuit array with a progressively decreasing radius.

Figure 26:
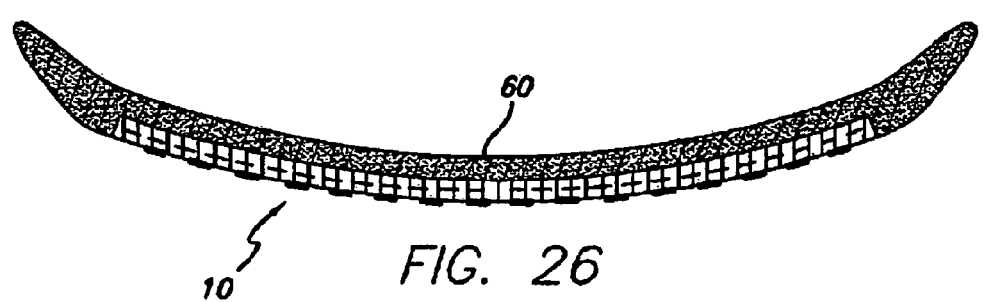
FIG. 26 depicts a flexible circuit array with a protective skirt bonded to the back side of the flexible circuit array and molded around the edges of the flexible circuit array and flush with the front side of the array with a progressively decreasing radius.

FIG. 26 depicts a flexible circuit array 10 with a protective skirt 60 bonded to the back side of the flexible circuit array 10 and molded around the edges of the flexible circuit array and flush with the front side of the array with a progressively decreasing radius.

Figure 27:
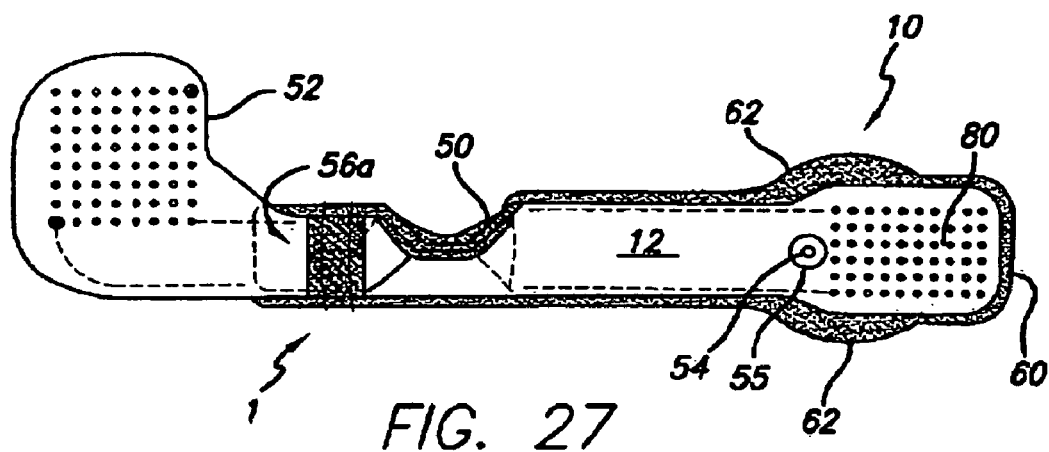
FIG. 27 depicts a plan view of the flexible circuit array with a skirt containing a grooved and rippled pad instead of a suture tab.
Figure 28:
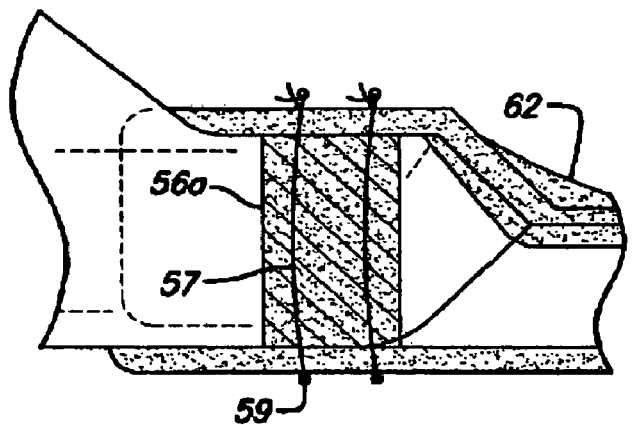
FIG. 28 depicts an enlarged plan view of a portion of the skirt shown in FIG. 27 containing a grooved and rippled pad and a mattress suture.

FIG. 27 depicts a plan view of the array with a skirt 60 containing a grooved and rippled pad 56a instead of a suture tab 56. This pad 56a has the advantage of capturing a mattress suture 57. A mattress suture 57 has the advantage of holding the groved or rippled pad 56a in two places as shown in FIG. 28. Each suture 57 is fixed on the tissue on four places 59. A mattress suture 57 on a grooved or rippled mattress 56a therefore enhances stability.

Figure 29:
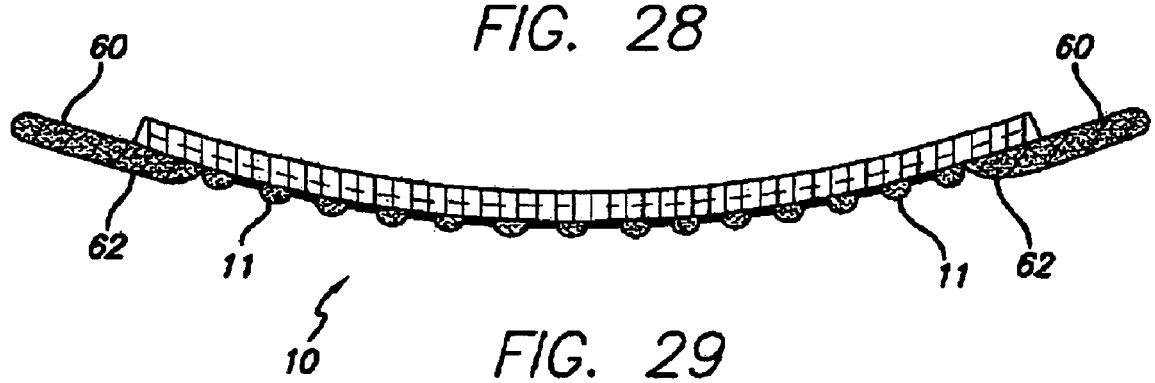
FIG. 29 depicts a flexible circuit array with a protective skirt bonded to the front side of the flexible circuit array with individual electrode windows.

FIG. 29 depicts in cross-section a flexible circuit array 10 with a protective skirt 60 bonded to the front side of the flexible circuit array 10 with individual electrode windows 62 and with material, preferably silicone, between the electrodes 11.

Figure 30:
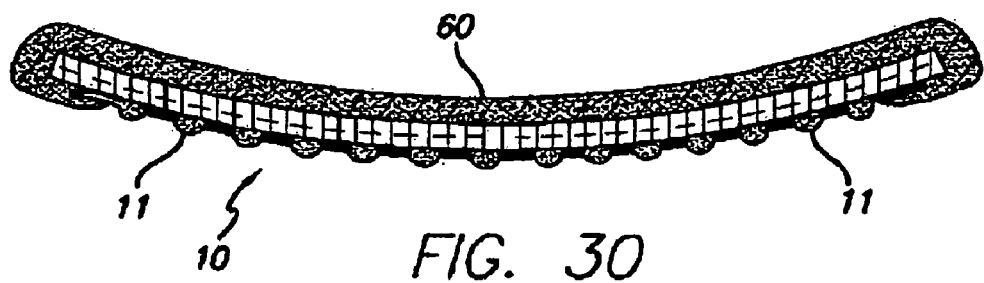
FIG. 30 depicts a flexible circuit array with a protective skirt bonded to the back side of the flexible circuit array and molded around the edges of the flexible circuit array with individual electrode windows.

FIG. 30 depicts in cross-section a flexible circuit array with a protective skirt bonded to the back side of the flexible circuit array and molded around the edges of the flexible circuit array with individual electrode windows and with material, preferably silicone between the electrodes 11.

FIGS. 31-36 show several surfaces to be applied on top of the cable. The surfaces are thin films containing a soft polymer, preferably silicone. FIG. 31 shows a flange 15: A flange 15 can be a solid film of material containing silicone added to the surface of the polymer containing polyimide. FIGS. 32-34 show a ladder 15a: A ladder 15a is a flange with material removed from central portions in some shape 19. FIG. 35 shows a skeleton structure 15b. A skeleton 15b is a flange with material removed from perimeter portions in some shape 21. FIG. 36 shows a structure 15c with beads 23 and bumpers 25. A bead 23 is material added to perimeter portions of the polymer cable in some shape without material being added on the central area. A bumper 25 can be an extended or continuous version of the beaded approach. Both embodiments are helpful in preventing any possible injury of the tissue by the polymer.

Figure 37:
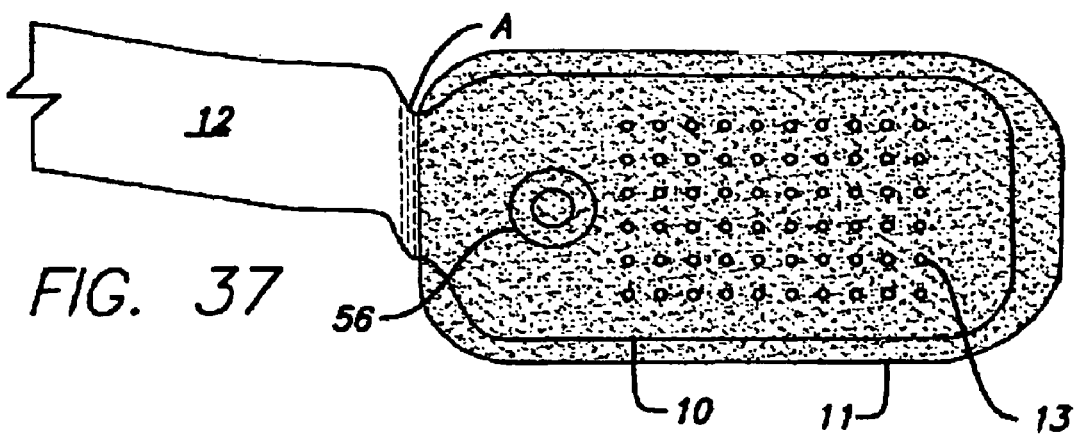
FIG. 37 depicts the top view of the flexible circuit array being enveloped within an insulating material.

FIG. 37 depicts the top view of the flexible electrode array 10 being enveloped within an insulating material 11. The electrode array 10 comprises oval-shaped electrode array body 10, a plurality of electrodes 13 made of a conductive material, such as platinum or one of its alloys, but that can be made of any conductive biocompatible material such as iridium, iridium oxide or titanium nitride. The electrode array 10 is enveloped within an insulating material 11 that is preferably silicone. "Oval-shaped" electrode array body means that the body may approximate either a square or a rectangle shape, but where the corners are rounded. This shape of an electrode array is described in the U.S. Patent Application No. 20020111658, entitled "Implantable retinal electrode array configuration for minimal retinal damage and method of reducing retinal stress" and No. 20020188282, entitled "Implantable drug delivery device" to Rober J. Greenberg et al., the disclosures of both being incorporated herein by reference.

The material body 11 is made of a soft material that is compatible with the electrode array body 10. In a preferred embodiment the body 11 made of silicone having hardness of about 50 or less on the Shore A scale as measured with a durometer. In an alternate embodiment the hardness is about 25 or less on the Shore A scale as measured with a durometer.

Figure 38:
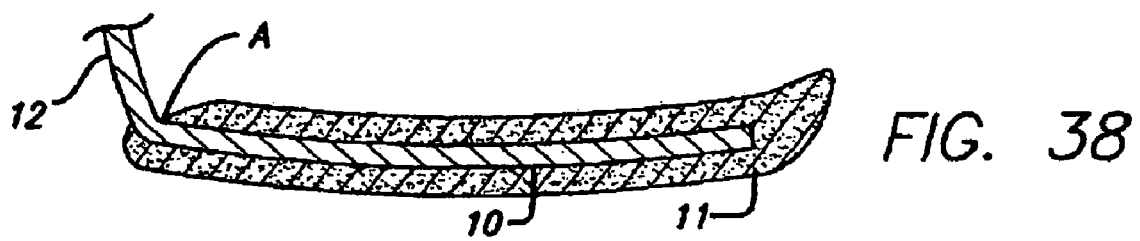
FIG. 38 depicts a cross-sectional view of the flexible circuit array being enveloped within an insulating material.

FIG. 38 depicts a cross-sectional view of the flexible circuit array 10 being enveloped within an insulating material 11. The figure shows how the edges of the material body 11 are lifted off due to the contracted radius. The electrode array 10 preferably also contains a fold A between the cable 12 and the electrode array 10. The angle of the fold A secures a relief of the implanted material.

Figure 39:
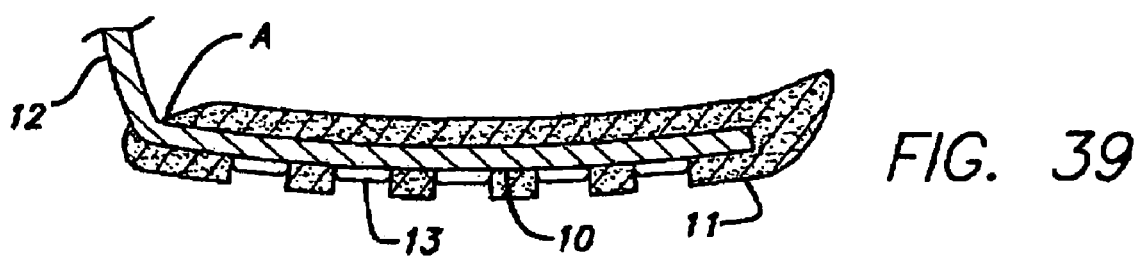
FIG. 39 depicts a cross-sectional view of the flexible circuit array being enveloped within an insulating material with open electrodes and insulating material between the electrodes.

FIG. 39 depicts a cross-sectional view of the flexible circuit array 10 being enveloped within an insulating material 11 with open electrodes 13 and the material 11 between the electrodes 13. This embodiment also has relief between the body 10 and the retina.

Figure 40:
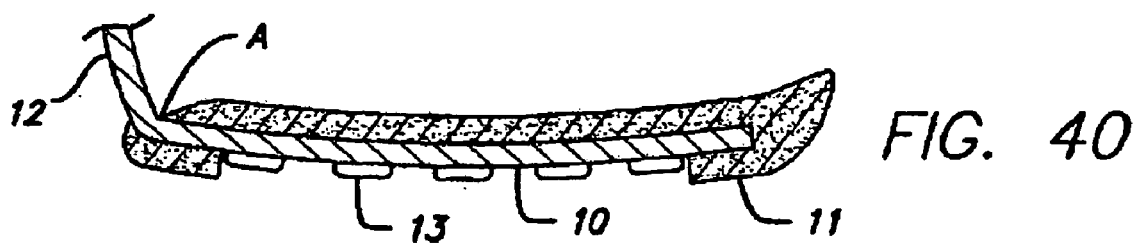
FIG. 40 depicts a cross-sectional view of the flexible circuit array being enveloped within an insulating material with open electrodes.

FIG. 40 depicts a cross-sectional view of the flexible circuit array 10 being partially enveloped within an insulating material 11 with open electrodes 13. This is another embodiment wherein the electrodes 13 are not separated by the material 11 but the material 11 is extended so that the electrodes 13 are prevented from directly contacting the retina.

Figure 41:
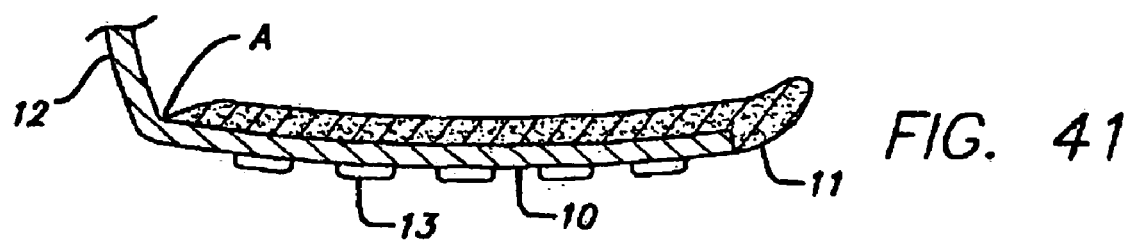
FIG. 41 depicts a cross-sectional view of the flexible circuit array being enveloped within an insulating material with electrodes on the surface of the material.

FIG. 41 depicts a cross-sectional view of the flexible circuit array 10 being enveloped within an insulating material 11 with electrodes 13 on the surface of the material 11. This is a further embodiment with the electrode 13 on the surface of the material 11, preferably silicone. The embodiments shown in FIGS. 39, 40, and 41 show a preferred body 11 containing silicone with the edges being lifted off from the retina due to contracted radius of the silicone body 11.

Figure 42:
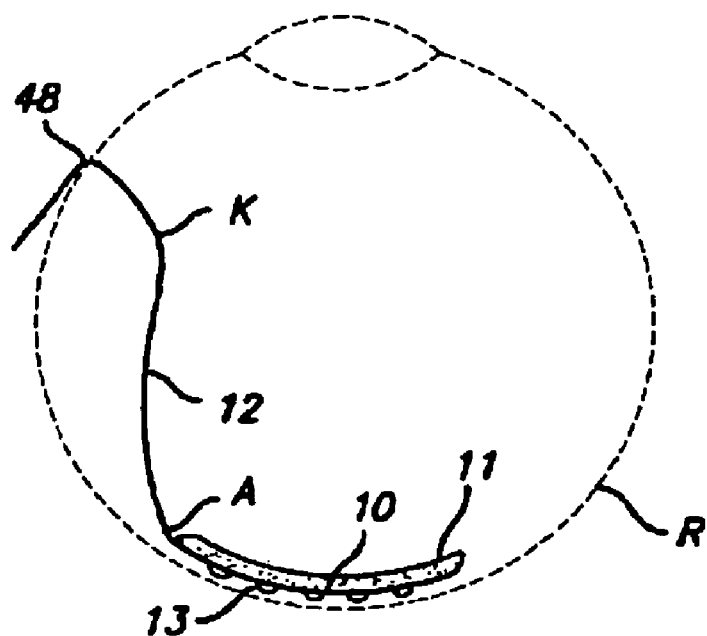
FIG. 42 depicts a cross-sectional view of the flexible circuit array being enveloped within an insulating material with electrodes on the surface of the material inside the eye with an angle in the fold of the flexible circuit cable and a fold between the circuit electrode array and the flexible circuit cable.

FIG. 42 depicts a cross-sectional view of the flexible circuit array 10 being enveloped within an insulating material 11 with electrodes 13 on the surface of the material 11 inside the eye with an angle K in the fold of the flexible circuit cable 12 and a fold A between the circuit electrode array 10 and the flexible circuit cable 12. The material 11 and electrode array body 10 are in intimate contact with retina R. The surface of electrode array body 10 in contact with retina R is a curved surface having edges with a contracted radius compared to the spherical curvature of retina R to minimize stress concentrations therein. Further, the decreasing radius of spherical curvature of material 11 near its edge forms edge relief that causes the edges of the body 11 to lift off the surface of retina R, eliminating stress concentrations. The edges of body 11 are strongly lifted off due to the contracted radius of the body 11. The edge of body 11 has a rounded edge eliminating stress and cutting of retina R.

Figure 43:
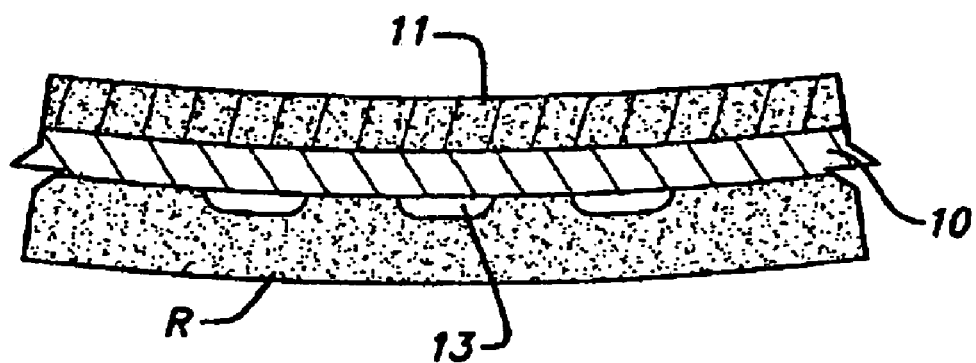
FIG. 43 depicts an enlarged cross-sectional portion side view of the flexible circuit array being enveloped within an insulating material with electrodes on the surface of the material inside the eye.

FIG. 43 shows a part of the FIG. 42 enlarged showing the electrode array 10 and the electrodes 13 enveloped by the polymer material, preferably silicone 11 being attached to the retina R.

The electrode array 10 embedded in or enveloped by the polymer material, preferably silicone 11 can be preferably produced through the following steps. The soft polymer material which contains silicone is molded into the designed shape and partially hardened. The electrode array 10 which preferably contains polyimide is introduced and positioned in the partially hardened soft polymer containing silicone. Finally, the soft polymer 11 containing silicone is fully hardened in the designed shape enveloping the electrode array 10. The polymer body 11 has a shape with a contracted radius compared with the retina R so that the edges of the body 11 lift off from the retina R.

Figure 44:
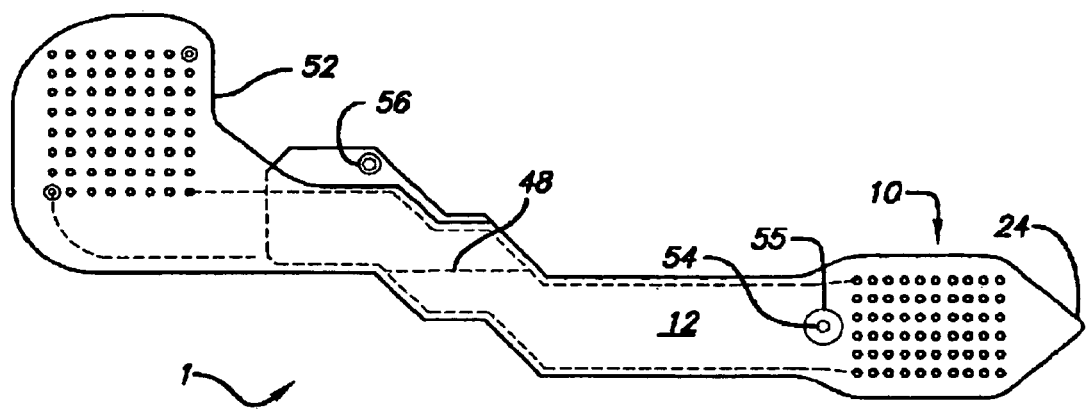
FIG. 44 shows the flexible circuit array before it is folded and attached to the implanted portion.

FIG. 44 shows the flexible circuit electrode array prior to folding and attaching the array to the electronics package 14. At one end of the flexible circuit cable 12 is an interconnection pad 52 for connection to the electronics package 14. At the other end of the flexible circuit cable 12 is the flexible circuit electrode array 10. Further, a point 24 is provided at the end of the flexible circuit electrode array 10. The flexible circuit cable 12 is formed in a dog leg pattern so than when it is folded at fold 48 it effectively forms a straight flexible circuit cable 12 with a narrower portion at the fold 48 for passing through the sclerotomy.

Figure 45:
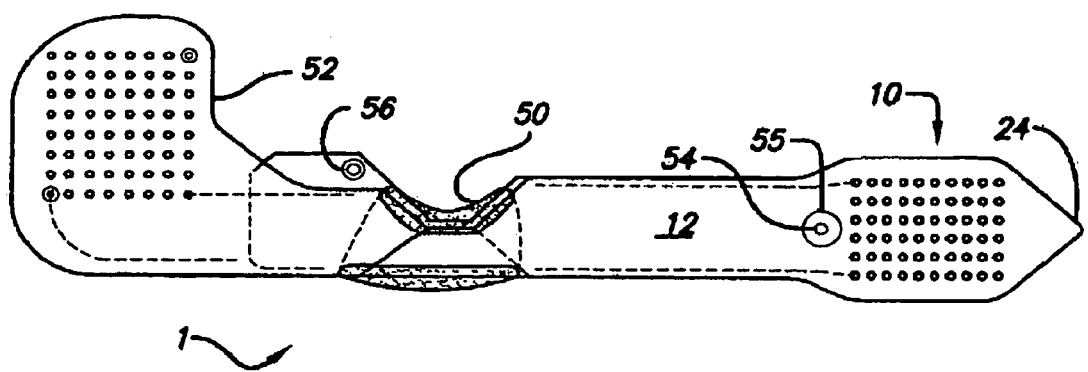
FIG. 45 shows the flexible circuit array folded.

FIG. 45 shows the flexible circuit electrode array after the flexible circuit cable 12 is folded at the fold 48 to form a narrowed section. The flexible circuit cable 12 may include a twist or tube shape as well. With a retinal prosthesis as shown in FIG. 1, the bond pad 52 for connection to the electronics package 14 and the flexible circuit electrode array 10 are on opposite side of the flexible circuit. This requires patterning, in some manner, both the base polymer layer and the top polymer layer. By folding the flexible circuit cable 12 of the flexible circuit electrode array 10, the openings for the bond pad 52 and the electrodes are on the top polymer layer and only the top polymer layer needs to be patterned. Further, a point 24 is provided at the end of the flexible circuit electrode array 10. The point 24 shown in FIGS. 2 and 3 is formed throughout the whole thickness of the array. The array may contain at least one bottom layer containing at least one polymer, copolymer, blockcopolymer or mixtures thereof and at least one top layer containing at least one polymer, copolymer, blockcopolymer or mixtures thereof. The polymer may be polyimide, silicone, PEEK polymer, a repeat unit that comprises of oxy-1,4-phenylenoeoxy-1,4-phenylene-carbonyl-1,4-phenylene, parylene or mixtures thereof.

Also, since the narrowed portion of the flexible circuit cable 12 pierces the sclera, shoulders formed by opposite ends of the narrowed portion help prevent the flexible circuit cable 12 from moving through the sclera. It may be further advantageous to add ribs or bumps of silicone or similar material to the shoulders to further prevent the flexible circuit cable 12 from moving through the sclera.

Further it is advantageous to provide a suture tab 56 in the flexible circuit body near the electronics package to prevent any movement in the electronics package from being transmitted to the flexible circuit electrode array 10. Alternatively, a segment of the flexible circuit cable 12 can be reinforced to permit it to be secured directly with a suture. The retina tack (not shown) is placed through an attachment point 54 to hold the flexible circuit electrode array 10 to the retina. A stress relief 55 can be made of a softer polymer than the flexible circuit 1.

Figure 46:
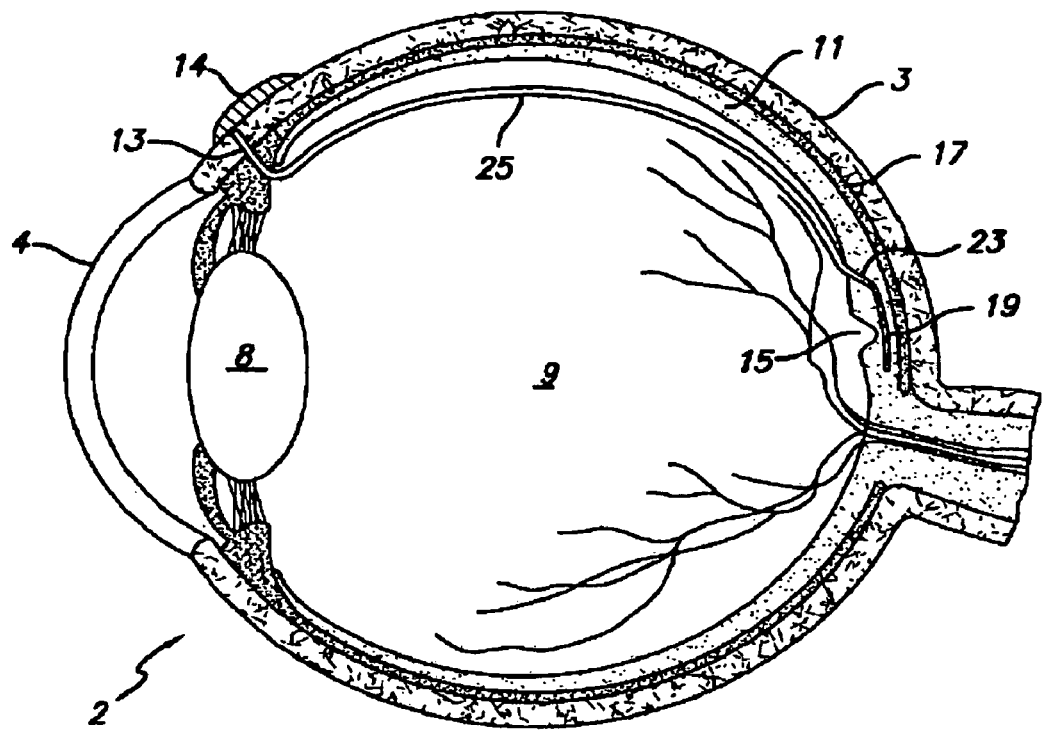
FIG. 46 shows a cross-sectional view of an eye showing the placement of the retinal implant and associated electronics.

FIG. 46 provides a cross-sectional view of a preferred embodiment of the eye 2 with a retinal implant 19 placed subretinally. The current invention involves the use of an electronic device, a retinal implant 19 that is capable of mimicking the signals that would be produced by a normal inner retinal photoreceptor layer. When the device is implanted subretinally between the inner and outer retinal layers, it will stimulate the inner layer to provide significantly useful formed vision to a patient who's eye no longer reacts to normal incident light on the retina 20. Patient's having a variety of retinal diseases that cause vision loss or blindness by destruction of the vascular layers of the eye, including the choroid, choriocapillaris, and the outer retinal layers, including Bruch's membrane and retinal pigment epithelium. Loss of these layers is followed by degeneration of the outer portion of the inner retina, beginning with the photoreceptor layer. The inner retina, composed of the outer nuclear, outer plexiform, inner nuclear, inner plexiform, ganglion cell and nerve fiber layers, may remain functional. Functioning of the inner retina allows electrical stimulation of this structure to produce sensations of light or even vision.

The biocompatible retinal implant 19 is attached by an electrically conductive cable or lead wire 25 that is also biocompatible, to a control electronics 14 package that contains suitable electronics to generate an electrical signal that is transmitted along a lead wire 25 to the retinal implant, which stimulates the retina 11. The lead wire 25 passes transretinally through retinal incision 13 and enters the vitreous cavity 9. The lead wire 25 then passes transsclera at sclera incision 13 that passes through the sclera at a location near the front of the eye where there is no retina 11.

The eye 2 has a cornea 4, lens 8, and vitreous cavity 9 through which light normally passes, prior to striking the retina 11 and causing vision. The eye 2 has an outer layer, called the sclera 6, and a nutrient rich layer, called the choroid 18, that is located between the retina 11 and the sclera 6.

In a preferred embodiment, the retinal implant 20 is located subretinally near the fovea 15 to provide good electrical contact between the retinal implant 19 and the retina 11. The lead wire 25, which is attached to the retinal implant 19, proceeds transretinally through retina 11 via retinal incision 23. Passing the lead wire into the vitreous cavity 9 via the retinal incision 23 avoids disrupting the delicate choroid 17, and thereby avoids interfering with the supply of nutrients to the retina 11. The lead wire 25 passes through the vitreous cavity to a point near the front of the eye 2 where it traverses transsclera via an incision 13 through the sclera 6 at a point where the retina 11 and choroid 17 are not present, thereby further avoiding disruption to the blood supply, oxygen, and nutrients that are needed to sustain the retina 11. While the choroid 17 does extend to this region of the eye near the lens 8, called the pars plana, choroid 17 bleeding will not damage the retina 11, and is far less likely to spread to the central retina 11, called the macula, which is the area of most sensitive vision, while choroid 17 bleeding under the retina 11 can track along the retina 11 and end up damaging the macular region near the fovea 19 of the retina 11.

The control electronics 14 are located outside the eye 2 and are attached to lead wire 25. The control electronics 14 are preferably attached to the sclera 6 by sutures. In alternative embodiments, the control electronics 14 are located distant from the eye 2.

Figure 47:
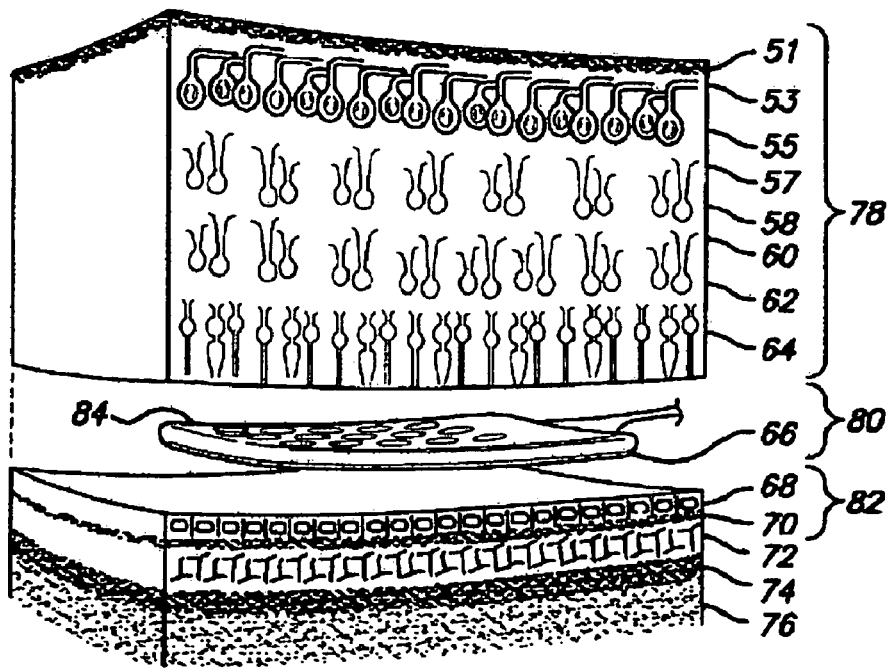
FIG. 47 shows a cross-sectional view of a retina showing the tissue layers and placement of the retinal implant in the retina for electrical stimulation of the retina.

A perspective cross-sectional view of the retina and outer wall of the eye is presented in FIG. 47. Moving from the inside of the eye outward, the structure of the eye is encountered as follows: internal limiting membrane 51, axons 53, ganglion and amacrine cell layer 55, inner plexiform 57, inner nuclear layer 58, outer plexiform layer 60, bipolar cell layer 62, photoreceptor cell layer 64, retinal pigment epithelium 68, Bruck's membrane 70, choriocapillaris 72, choroid 74, and the outer coat or sclera 76.

The inner retina 78 is generally the structures from the internal limiting membrane 50 to the photoreceptor cell layer 64. The outer retinal layer is the retinal pigment epithelium 68 and Bruck's membrane 70.

A subretinal implant position 80 is located between the photoreceptor cell layer 64 and the retinal pigment epithelium 68. In a preferred embodiment, the retinal implant 66 is surgically implanted in the subretinal implant position 80.

In a preferred embodiment, the retinal implant 66 is biocompatible and contains a number of arrayed electrodes 84, which are electrically stimulated by an outside source to stimulate the inner retinal layer 78, thereby to provide significantly useful formed vision. It is preferred that the electrodes 84 are located on the surface of the retinal implant 66 that faces the front of the eye, to stimulate the inner retinal layer 78.

Figure 48:
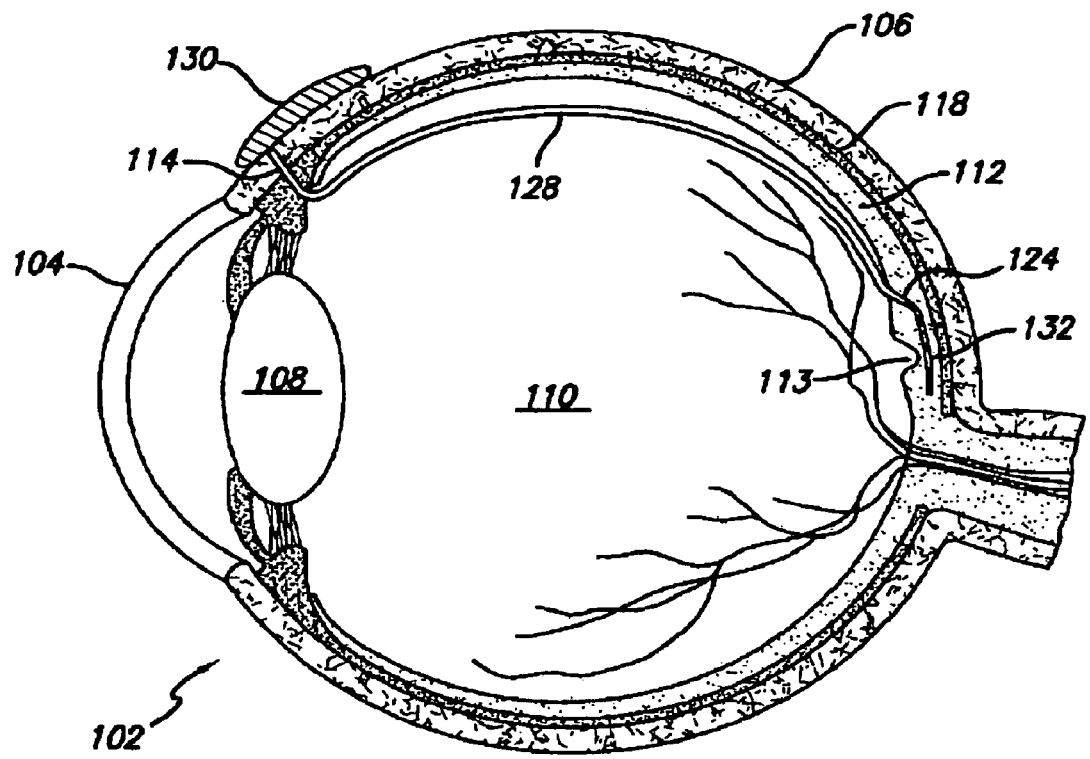
FIG. 48 shows a cross-sectional view of an eye showing placement of the retinal implant for drug delivery.

A cross-sectional view of the eye 102 and retinal implant 132 is presented in FIG. 48. In this embodiment of the invention, drugs are delivered by transfer from drug reservoir 130 to retinal implant 132, where the drugs are released subretinally for treatment of the tissue of the eye 2 and especially the retinal tissue. This device is particularly advantageous for treatment of chronic issues. A further advantage is that the quantity of drugs required and released to the eye is minimized by releasing the drugs in near proximity to the area of the eye 102 that requires treatment.

In a preferred embodiment, the drugs are transferred from drug reservoir 130 via delivery conduit 128, which is preferably a tube, to retinal implant 132. While the drugs may be pumped or delivered by other known means, it is preferable that they be delivered electrophoretically.

The structure of the eye 2, as shown in FIG. 48, presents a cornea 104 at the front of the eye with a lens 108 behind. The sclera 106 is on the outside of the eye and the choroid 118 is inside the eye 2 between the retina 112 and sclera 106.

The retinal implant 132 is implanted subretinally, preferably near the back of the eye. It is shown near the fovea 113, in FIG. 48, but may be located at other subretinal locations, as desired. The drug delivery conduit 128 connects the retinal implant 132 with the drug reservoir 130. The conduit 128 passes transretinally through retinal incision 124 and enters the vitreous cavity 110. The conduit 128 then passes transsclera at sclera incision 114 that passes through the sclera at a location near the front of the eye where there is no retina 112, thereby avoiding damage to the nutrient rich choroid 118 and avoiding disruption of the blood supply to the retina 112.

Figure 49:
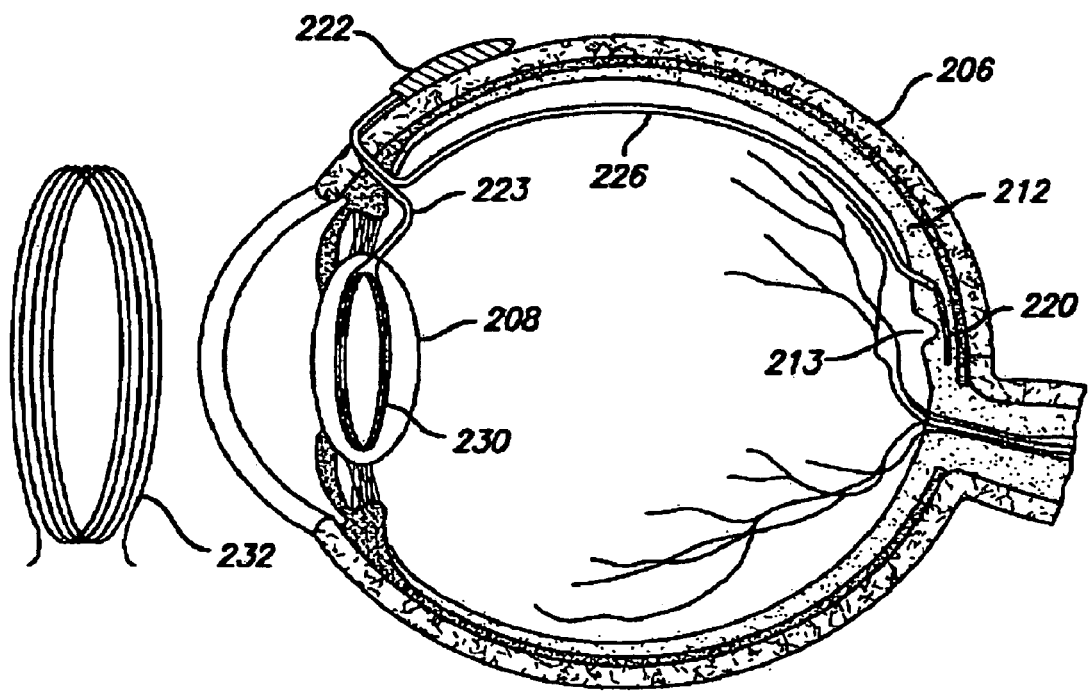
FIG. 49 shows a cross-sectional view of an eye showing the placement of the subretinal implant.

An alternative embodiment of a retinal implant to enable vision restoration is presented in FIG. 49, wherein a cross-section of the eye is presented showing the lens 208, retina 212, sclera 206, and fovea 213. U.S. Pat. No. 5,935,155, issued to Humayun, et al., the '155 patent, describes a similar visual prosthesis and method of use. In this embodiment, the retinal implant 220 is implanted subretinally. A primary coil 232 is located preferably either in an eyeglass lens frame or in a soft contact lens. This coil 232 is used to inductively couple the radio frequency encoded image signal to the secondary coil 230 that, in this embodiment, is implanted behind the iris of the eye. The control electronics 222 is placed in a hermetically sealed package and is coupled to a secondary coil 230 by a coil lead 223 that pierces the sclera 206 at a point near the lens 208 where there is no retina 212. The control electronics 222 is attached to the outside of the sclera 206. A lead wire 226 coupling the control electronics 222 to the retinal implant 220 passes transsclera at a point where there is no retina, preferably near the lens 208. The lead wire 226 passes inside the eye, preferably along the interior wall of the eye, and pierces the retina to pass transretinal to couple the control electronics 222 to the retinal implant 220. This invention is an improvement over that disclosed by the '155 patent because the retinal implant is subretinal rather than epiretinal, thereby facilitating stimulation of the retinal tissue.

Figure 50:
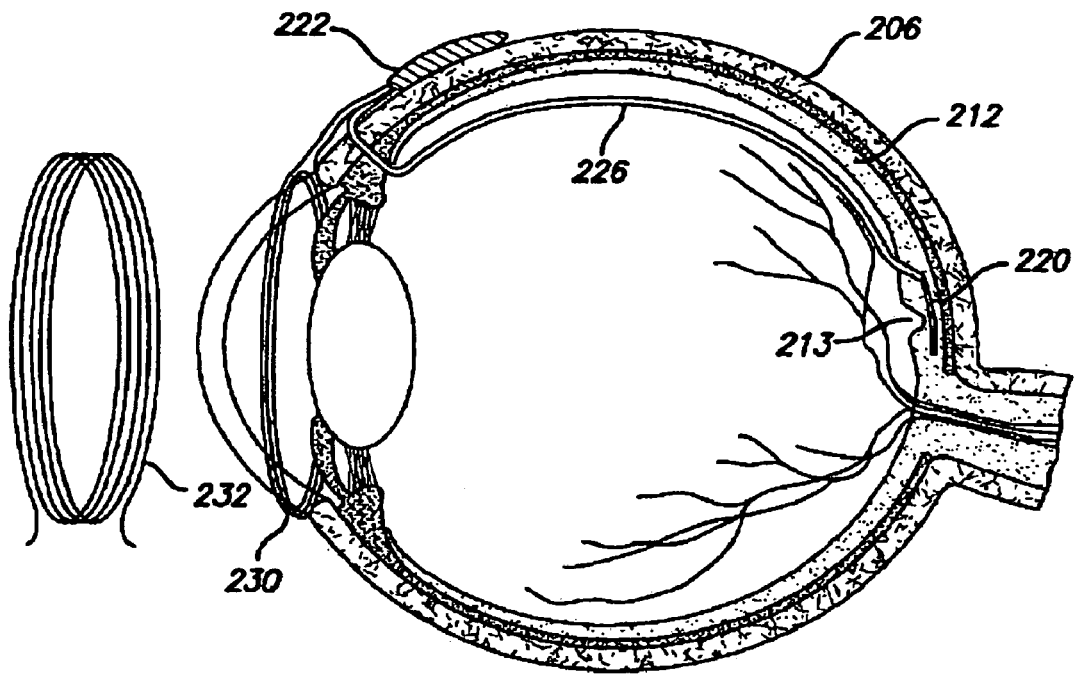
FIG. 50 shows a cross-sectional view of an eye showing the placement of the subretinal implant.

A further alternative embodiment of a retinal implant to enable vision restoration is presented in FIG. 50. The '155 patent discloses a similar invention, wherein the retinal implant 220 is placed subretinally. In this embodiment, the secondary 230 is attached to the sclera 206 instead of being implanted within the eye. As with the control electronics 222, the attachment of the secondary coil 230 to the sclera 206 may be by suturing or other appropriate means, as discussed in the '155 patent. In this way, only the lead wire 226 which attaches the control electronics 222 to the retinal implant 220 mounted subretinally below retina 212 is required to pierce the sclera 206. The extra-ocular attachment of the control electronics 222 allows increased access to this circuitry that eases the replacement or updating of these components.

Figure 51:
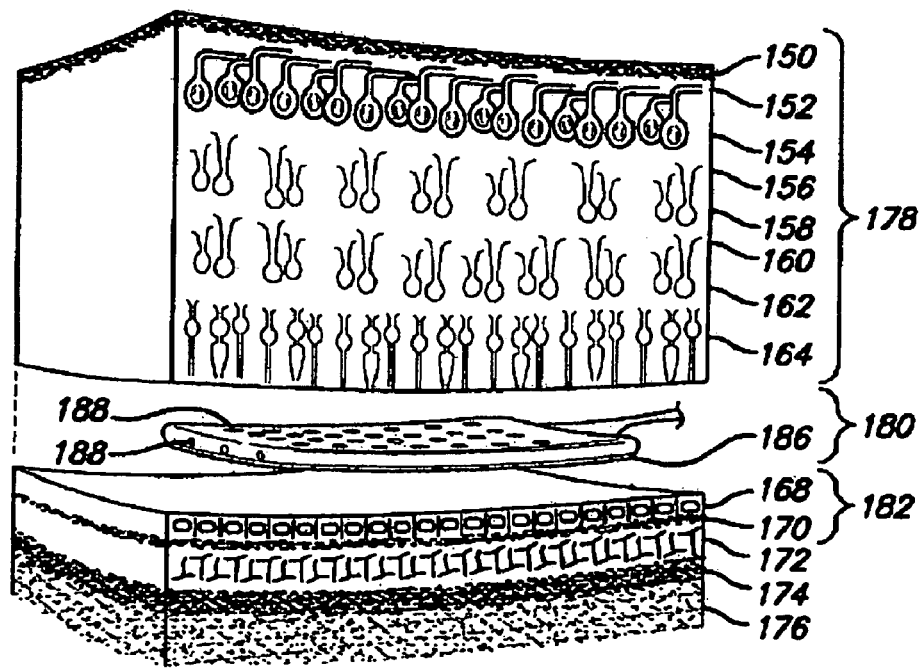
FIG. 51 shows a cross-sectional view of a retina showing the tissue layers and placement of the retinal implant in the retina for drug delivery.

FIG. 51 presents a perspective cross-sectional view of the retina and outer wall of the eye. The tissue layers from the inside of the eye outward are the internal limiting membrane 150, axons 152, ganglion and amacrine cell layer 154, inner plexiform 156, inner nuclear layer 158, outer plexiform layer 160, bipolar cell layer 162, photoreceptor cell layer 164, retinal pigment epithelium 168, Bruck's membrane 170, choriocapillaris 172, choroid 174, and sclera 176.

The inner retinal layer 178 is comprised of tissue from the internal limiting membrane 150 to the photoreceptor cell layer 164. The outer retinal layer 182 consists of the retinal pigment epithelium 168 and Bruck's membrane 170.

Between the inner retinal layer 178 and outer retinal layer 182, is the subretinal implant position 180 in which retinal implant 186 is surgically located.

The retinal implant contains a number of orifices 188 through with the drug is released into the surrounding retinal tissue. The orifices 188 are preferably uniformly presented on both the inner and outer surfaces as well as on the edges of the retinal implant 186. However, the orifices 188 may be preferentially oriented in the retinal implant 186 to selectively release the drug on or near a desired tissue or location.

Figure 52:
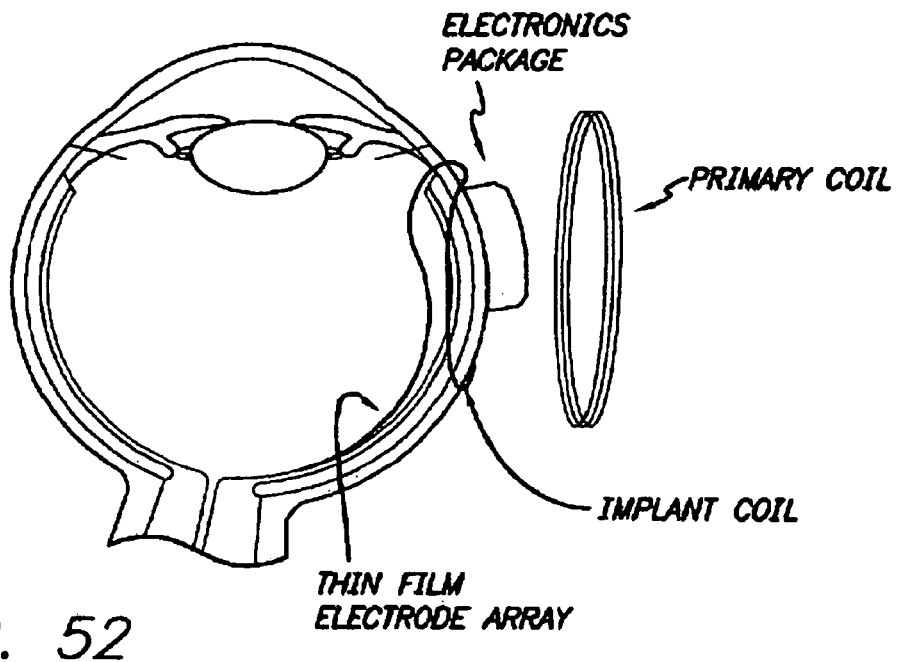
FIG. 52 shows a cross-sectional view of the eye with the preferred retinal prosthesis.

A fully functional and long-lasting device, composed of the implant and external system, is shown in FIG. 52. There is an extra-ocular electronics package and secondary coil connected to a thin film electrode array that runs through a pars plana incision into the eye where the array is tacked onto the retina or placed subretinally through a retinotomy.

The retinal electrophysiology and human clinical testing are designed to provide valuable information required to make device development decisions. In some cases, device performance is limited by physical and electrical constraints—i.e. material charge density limits or voltage limits in today's integrated circuit technology. In other cases it is limited by the biology—i.e. tissue damage tolerance evaluated above, retinal biology, or eye movements.

Multi-electrode array recordings will allow us to measure thresholds for activation of single or larger collections of ganglion cells. Preliminary experiments have shown that threshold stimulation using 10-15 μm electrode diameters activates one or a few ganglion cells located within 60 μm of the stimulation site. By incorporating Second Sight manufactured electrode arrays with different sized electrodes into the Salk Institute's multi-electrode recording system, it will be able to record ganglion cell responses to stimulation with a wide range of stimulating electrode diameters 5-500 μm.

The literature analysis of charge thresholds shown in FIG. 56 suggests that with decreasing electrode size, the required charge density does not significantly increase. The multi-electrode experiments in degenerate retina further show that electrodes with diameters of 10-20 μm reliably stimulate individual ganglion cells in normal and degenerate rat retina at charge densities below 0.2 mC/cm$^2$. Thus, stimulation with small-diameter electrodes is likely to be both safe and effective when using platinum gray electrodes. The electrode spacing is in the 5-500 μm range.

The simultaneous stimulation of two or more very small electrodes spaced 60 μm apart results in independent activation of ganglion cells near each stimulation site. Increasing the number of place-pitch steps a factor of 2-9× over single electrodes available to cochlear implant listeners.

The proportion of the total current directed to each electrode will vary between p=1 only the first electrode stimulated to p=0 only the second of the two electrodes stimulated. If both electrodes are stimulated with equal amounts of current, normalized for electrode sensitivity, presented to each electrode then, p=0.5. On each trial, multiple stimuli p=1, p=0.5 or p=0 separated in time will be presented in random order, and the subject asked to press a key every time the stimulus appears further to the right than the previous one assuming laterally adjacent electrodes. If this experiment results in the perception of three phosphenes that are distinctly located in space, then a second experiment will be conducted where more discrete levels for p are selected. Analysis of the function relating current ratio (p) to the perceived spatial position will be used to determine whether current steering can produce reliable shifts in the position of the resulting phosphene and how many intervening 'virtual electrodes' can be produced.

For an epiretinal prosthesis, the size of the electrode array is dictated by surgical concerns to about 5×6 mm. This is the area which fits comfortably between the large 'arcade' blood vessels which surround the macula. If an array were larger than this, blood flow to the distant retina might be compromised. It is currently unknown how large a subretinal array can be, but surgical limitations may limit its size to something similar.

The size of the overall array and the electrode center-to-center spacing dictate how many electrodes will fit in the given area. Obviously, the electrode size diameter must also be smaller than the center-to-center spacing.

Figure 53:
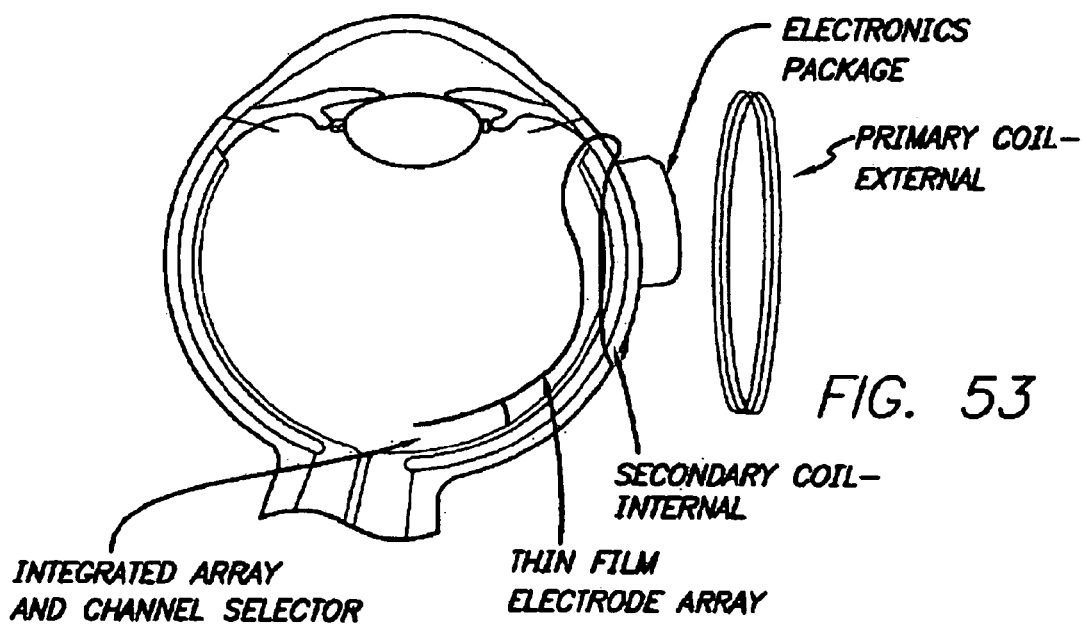
FIG. 53 shows a cross-sectional view of the eye with the preferred retinal prosthesis.

This design essentially employs an electronics package that supports 250 channels with a 1:4 electrode selector that is integrated into the array. Thus each driver can drive up to 4 electrodes at a time resulting in an implant that may support up to 1,000 electrodes, if necessary. FIG. 53 shows the epiretinal version, but the subretinal version will be similar with the cable passing through a retinotomy and the de-multiplexer inverted so that the electrodes face the retina. There are approximately 250 lines on the thin film cable running down the channel selector that is integrated onto the array.

If between 60 and 250 electrodes are needed, then the following three component technologies will be required:

(1) A thin-film array technology of sufficient density to permit routing to 250 electrodes. Sufficient improvements in density could come from process improvements mask and alignment resolution and an additional metal layer for the cable.

(2) An electronics package with up to 300 vias/cm$^2$ instead of the 100 vias/cm$^2$ that the implant contains.

(3) An ASIC driver for 250 individually addressable channels. This will be achieved through emerging packaging approaches and a change in the chip fabrication process to 0.6 um, 0.35 um or possibly smaller.

If more than 250 electrodes are needed, then three additional component technologies will be required:

(4) Development of an integrated array and channel selector IACS, including a means of forming the array. The IACS will contain a 1-to-4 channel demultiplexer and will have integrated electronics on the 'back' flat surface and electrodes on the 'front' formed surface. It is anticipated that the IACS will be made from silicon using a combination of standard micro-fabrication procedures to integrate the required electrical components and custom MEMS engineering to shape the array portion and provide electrical feedthroughs to the electrodes.

(5) Development of a low-profile package to protect the IACS. The IACS will be interconnected to the thin flexible cable described above using a platinum conductor technique developed during the first BRP period, but the IACS device itself needs to be packaged as it is well known that silicon degrades in the human body. It is not possible to put a massive package on the delicate retina, and so a thin film package<10 um is the preferred solution. In addition, the film can be patterned selectively to expose electrical contacts vias where required. Testing of this thin film package has demonstrated via densities of 25 vias/mm$^2$ and lifetimes in excess of 5 years in saline.

(6) Modifications to the 250 stimulator in order to support electrode selection. Control lines and circuits will be added to the 250-channel driver chip to control the IACS.

The implant is attached to the sclera using a 240 band and two sutures, and the electrode array and cable introduced into the eye through an enlarged supero-temporal sclerotomy. For an epiretinal approach the electrode array is tacked over the area centralis, while for a subretinal approach the array is inserted under the area centralis through a retinotomy. The sclerotomies and conjuctiva are closed and steroids and antibiotics are injected. The animals are provided analgesia for 48 hours post-operatively. Prophylactic antibiotics and systemic steroid are provided over 2 weeks postoperative.

Electrophysiology—Patch pipettes will be used to make small holes in the inner limiting membrane and ganglion cells will be targeted under visual control. Light responses will be used to assign the targeted cell to a known ganglion cell type. Spiking will be recorded with a cell-attached patch electrode 5-6 MΩ, filled with superfusate. Excitatory and inhibitory input currents will be measured with whole-cell patch clamp electrodes 6-7 MΩ.

Figure 54:
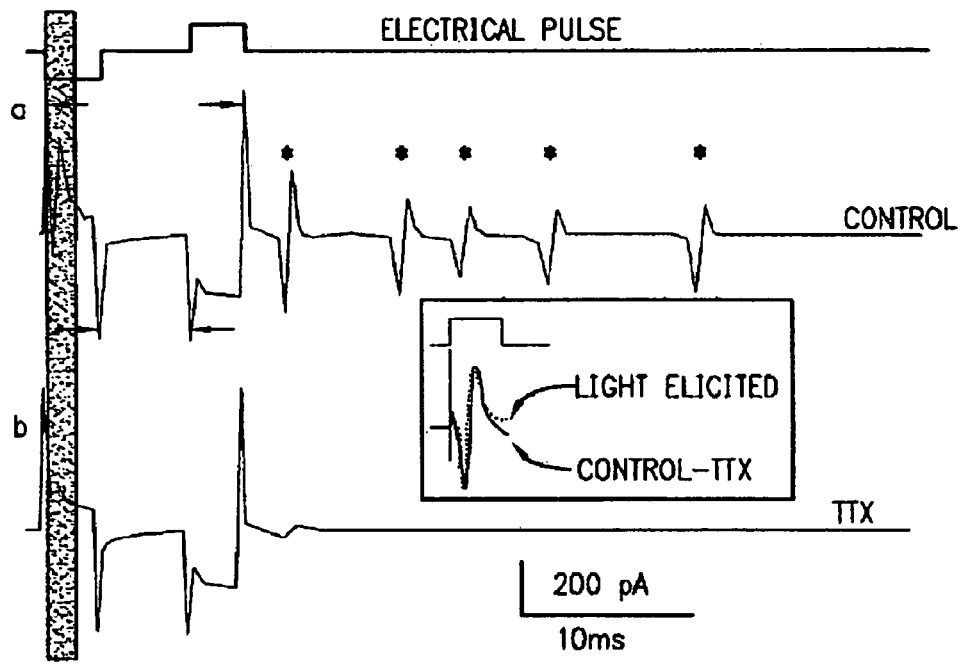
FIG. 54 shows stimulus pulses elicit 2 phases of neuronal spikes.

Distinguishing neural activity from stimulus artifact: The response to pulses of electrical current consists of large transient currents (FIG. 54a, horizontal arrows) that are temporally correlated with the onset and offset of both phases of the stimulus pulse cathodic and anodic. A series of biphasic waveforms (asterisks) follow the large transient currents. These biphasic waveforms have similar magnitudes and kinetics to light-elicited action potentials (FIG. 54 inset). FIG. 54: Stimulus pulses elicit 2 phases of neuronal spikes. (a) Biphasic stimulus pulse consisting of 3 ms cathodic phase, 5 ms inter-phase interval and 3 ms anodic phase timing at top elicits 5 biphasic waveforms (asterisks) in retinal ganglion cell. (b) TTX eliminates all biphasic waveforms indicating they are neuronal spikes. TTX also modulates the response in the region immediately following the onset of the cathodic pulse gray box. Subtraction of the TTX response from control indicates a single biphasic waveform (inset) that has similar kinetics and magnitude to the average light-elicited spike (dotted).

Tetrodotoxin (TTX), a blocker of neuronal spiking, eliminates the biphasic waveforms (n=5/5), confirming that they were conventional voltage-gated Na$^+$ spikes.

This suggests that one or more spikes are buried within this transient current. To reveal the spike(s) it is reasoned that the response in TTX did not contain neural activity and was therefore mainly electrical artifact generated by the stimulus pulse. Subtraction of the electrical artifact TTX response from the control response reveals an additional pulse-elicited spike (inset, solid trace, n=5/5). The waveform of this spike is nearly identical to the average light-elicited spike for this cell (inset, dotted trace). It is referred to this single spike as the 'early-phase' spike and referred to the subsequent series of multiple spikes biphasic waveforms as 'late-phase' spikes. Similar results are found in all ganglion cell types of the rabbit retina. The onset of the TTX-extracted pulse-elicited spike closely follows the onset of the cathodic pulse (mean=580 µs, range=400-680 µs, n=5). Without TTX, it is difficult to precisely determine the onset of the elicited spike, but comparison of control records in 5 TTX and 15 non-TTX experiments are similar, providing additional support that the elicited spike closely and consistently follows the stimulus pulse onset.

The multi-electrode retinal system consists of the following components: (1) a rectangular two-dimensional array of 512 planar microelectrodes with a sensitive area of 1.7 mm$^2$ in total, or an array of 61 electrodes arranged hexagonally, with an area of 0.25 mm$^2$. The preliminary data were gathered using the 61-electrode array. Each microfabricated platinum electrode is 5-15 microns in diameter and the electrode-electrode spacing is 30-60 microns. (2) custom-designed integrated circuits to pass current through the electrodes and AC couple their output signals; (3) integrated circuits to amplify, band-pass filter and multiplex the recorded signals; (4) a data acquisition system; and (5) data processing software.

Live retina is placed in a chamber, ganglion cell side down, on top of the array. The tissue is bathed continuously with a flow of oxygenated physiological saline solution, which allows the retina to be kept alive for up to 12 hours. The raw data recorded are the electrode voltage signals, digitized at 20 kHz: typically, each electrode picks up spikes from several neurons, and each neuron produces signals on several electrodes. For electrical stimulation, rectangular charge-balanced current pulses are applied through one or multiple electrodes; for visual stimulation, white noise or other stimuli are presented on a screen and optically focused on the retina. Extracellular spikes are identified based on their characteristic bi- or triphasic shape; electrically evoked spikes are by definition time-locked to the stimulus pulse by a latency of 0.2-15 milliseconds. Signals from all electrodes are stored for off-line analysis.

Figure 55:
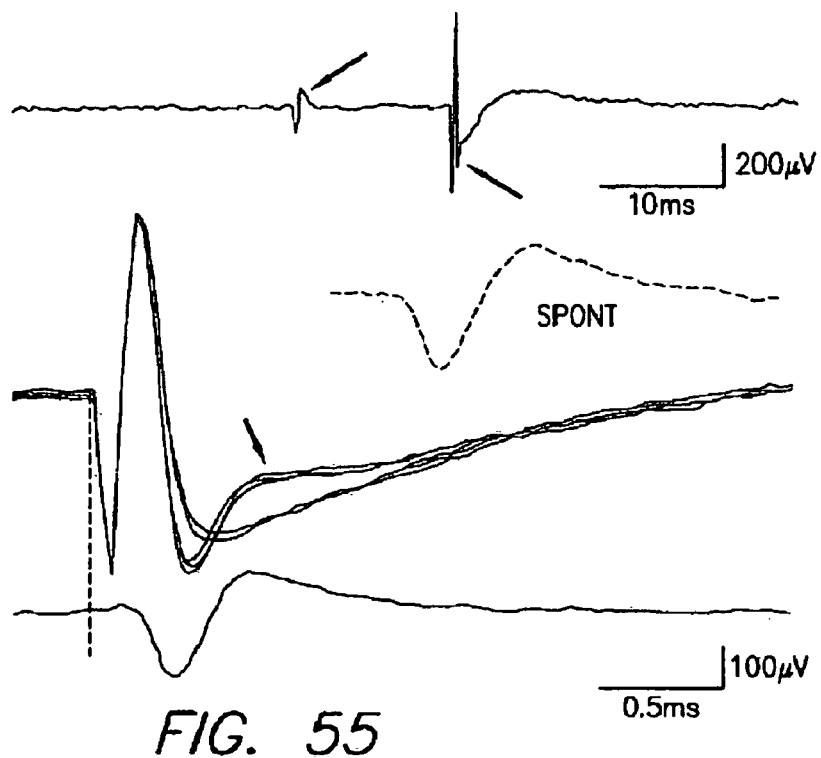
FIG. 55 shows a measurement of spontaneous spikes.

To distinguish neural responses from the electrical artifact, a novel method of threshold artifact subtraction will be employed, allowing evoked spikes to be recorded at latencies of a few hundred μs. It takes advantage of the fact that near threshold some stimulation trials will result in evoked spikes and some will fail to evoke responses. Subtracting the failures from the successful stimulations eliminates the artifact and cleanly reveals the recorded ganglion cell spike (see FIG. 55). FIG. 55 shows: Top example of a spontaneous spike (gray arrow) and an evoked spike (black arrow) which was hidden in the electrical artifact and required artifact subtraction to reveal. Bottom example is the same stimulation experiment at an expanded scale. A superposition of several stimulation trials is shown, some of which evoked a spike (arrow). Bottom trace is the digital subtraction of averaged traces from trials with and without an evoked spike. Vertical dashed line indicates stimulation onset. Latency=0.25 ms. Inset shows the spontaneous spike at the same scale for comparison.

Two interval forced choice technique subjects are presented with two intervals denoted by computer beeps, which contain different stimuli, and are forced to choose the stimulation interval, via a key-press that contains the brighter stimulus. This approach avoids response biases because if the stimuli presented in the two intervals are perceptually indistinguishable, then subjects will perform at chance in responding which interval contained the brighter stimulus. A correct response will be given auditory feedback with a beep.

The threshold is the stimulation intensity at which the subject performs at 50% correct, corrected for the false alarm rate in the case of the yes-no paradigm) and is 80% correct performance in the case of the procedure. Errors in the threshold estimation are characterized by the 90% confidence interval in which the "true" threshold value will fall.

Brightness or size matching—The subject is presented with two intervals: one containing a "standard" stimulation pulse whose parameters will remain fixed throughout the experiment and a second containing a "matching" stimulation pulse produced using different parameters. The subject selects the interval that contained the brighter stimulus. If they report that the matching pulse was brighter, its intensity will be reduced on the next trial. If they report that the standard pulse was brighter, the matching pulse's intensity will be increased on the next trial. The technique described above will be used to fit the data and the 50% correct value is considered the point of "subjective equality".

The height of the electrodes from the retinal surface can be measured by using optical coherence tomography (OCT). A cross-sectional image of the retina is taken using the optical backscattering of light. The opaque platinum electrodes cast broad shadows and the height of these shadows from the retinal surface can be measured. An image processing program has been developed that loads OCT images, determines the OCT pixel-micron conversion factor, identifies individual electrodes and measures electrode height and retinal thickness.

Eye movement recording—A video-based eye tracking system (Arrington Research) is used to record eye position, including nystagmus. Because the pupil position of blind subjects cannot be calibrated to the position of visual targets using usual techniques, a novel calibration technique is developed that maps the pupil position to the location of tactile calibration points across the visual field.

To determine the smallest safe electrode size for a high resolution prosthetic, it is necessary to know whether perceptual thresholds for electrical stimulation are determined by the amount of charge or the charge density. If thresholds are determined by the total charge, then the small electrodes required to increase spatial resolution are likely to result in charge densities that reach unacceptable levels. Charge thresholds generally decrease with electrode size. The solid line in FIG. 56 represents a line of constant charge density (0.2 $mC/cm^2$) which yields a correlation coefficient $R^2$=0.75. While larger electrodes clearly require higher charge injection for successful stimulation, the data points lie close to the line denoting constant charge density. These stimulation experiments in isolated retina show that spikes can be readily elicited in ganglion cells, even with very small electrodes, without exceeding the charge density limit for platinum gray electrodes (1.0 $mC/cm^2$). Solid circles denote the average data from 3 human subjects tested using 250 μm and 500 μm electrodes (means±standard deviation).

Recent threshold measurements in transgenic rats with severely degenerated retinas showed that spike thresholds in degenerated retina are not different from those of normal retina (FIG. 57). These findings suggest that very small electrodes can directly stimulate ganglion cells. Avarage threshold currents in normal (dark bars) and degenerated (light bars) retinal using 0.1 ms pulses (±SEM). Three electrode diameter ranges are shown. Number indicate numbers of stimulated cells. To verify this, blockers of synaptic transmission were added to the perfusion. Spike shapes, latencies, and response rates were unchanged in 9 cells tested (FIG. 58), indicating that ganglion cells were activated directly and not by presynaptic input from bipolar cells. Response to 10 stimulus pulses in a cell with spikes at latency 5.5 ms in rat retina. Bottom: A combination of glutamate receptor antagonists was added to the perfusion solution. The finding that thresholds are determined by charge density (FIG. 56), and our demonstration that these results also hold for degenerated retina (FIG. 58) suggest that it may indeed be possible to significantly reduce electrode sizes.

Three human subjects were implanted with a checkerboard style array containing electrodes alternating between 250 μm and 500 μm to determine if these electrode sizes resulted in different thresholds. Thresholds were measured using a biphasic charge balanced pulse 0.975 ms cathodic, 0.975 ms interpulse delay, 0.975 ms anodic. The checkerboard arrangement within individual subjects minimized the effects of any tilt of the array on the retinal surface or any differences between subjects in their state of retinal degeneration. A significant increase was observed in the amount of charge required to elicit a percept for the larger electrode size (FIG. 56, filled circles) as would be expected if thresholds were related to charge density.

Figure 59:
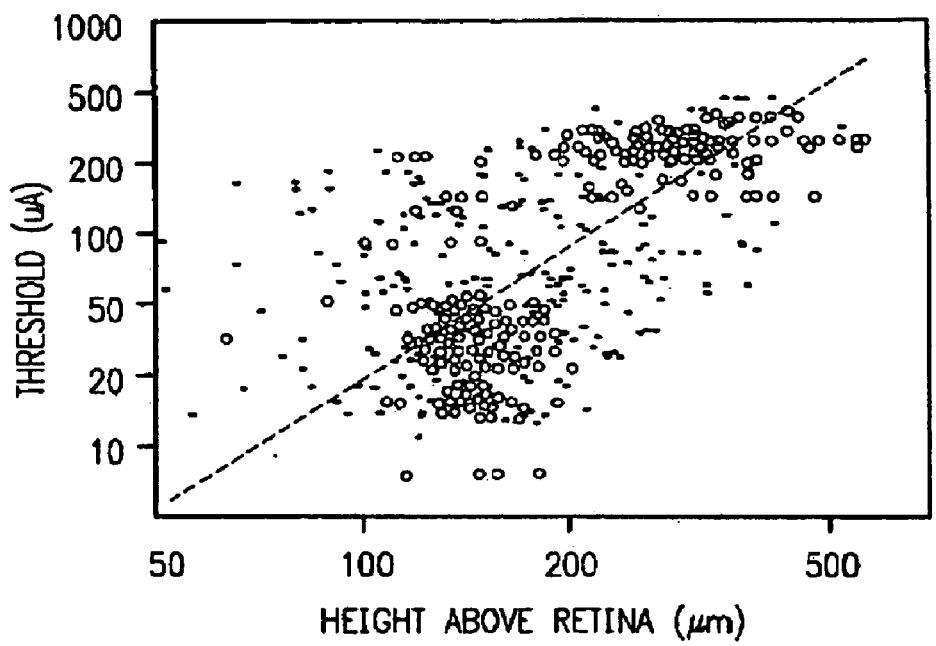
FIG. 59 shows a shows the correlation between height and electrical stimulation threshold in these 4 subjects.

FIG. 59 shows the correlation between height and electrical stimulation threshold in these 4 subjects. Close proximity of the array to the retinal surface yields lower stimulation thresholds. Thus, the electrode array should lie as close to the retinal surface as possible. Data in animals has consistently shown that the electrode surface is within 50 μm of the retina.

Figure 60:
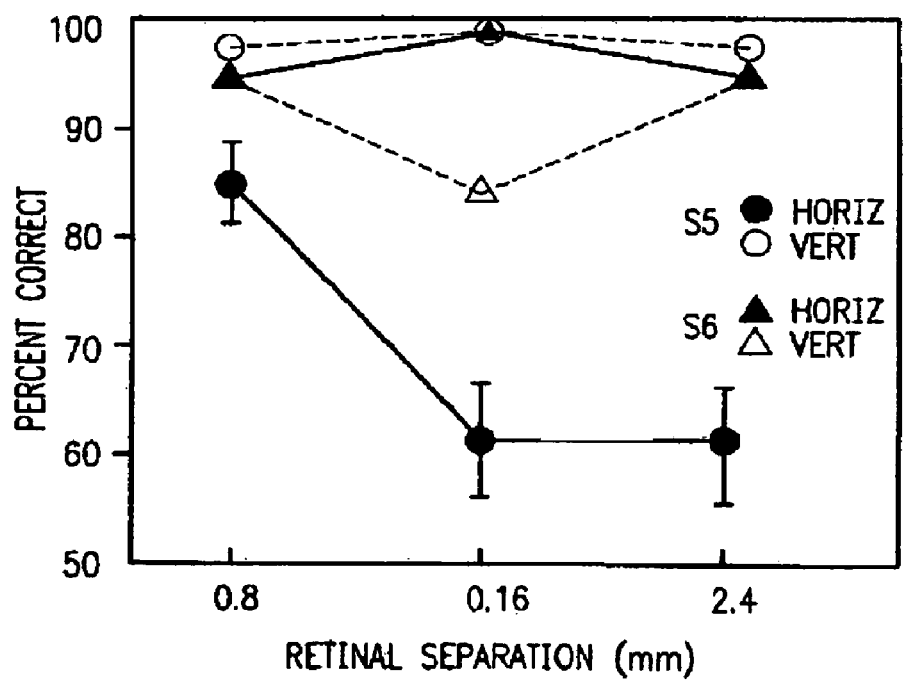
FIG. 60 shows a two point discrimination performance.

FIG. 60 shows the ability of two subjects to discriminate between a single stimulated electrode and a pair of stimulated electrodes. The currents needed to produce equal apparent brightness for the single pulse and the pulse pair were equalized prior to the start of the experiment and then the current was jittered on each trial to prevent subjects from using small brightness changes as a cue to perform the task. FIG. 60 shows a two-point discrimination performance. The x-axis represents the distance on the retina between the stimulated electrodes (1 mm on the retina is equivalent to 3° of visual angle). Performance is shown for two subjects; performance for horizontally (solid line) and vertically (dashed lines) aligned electrodes is shown separately. Error bars represent binominal error estimates of the mean.

Figure 61:
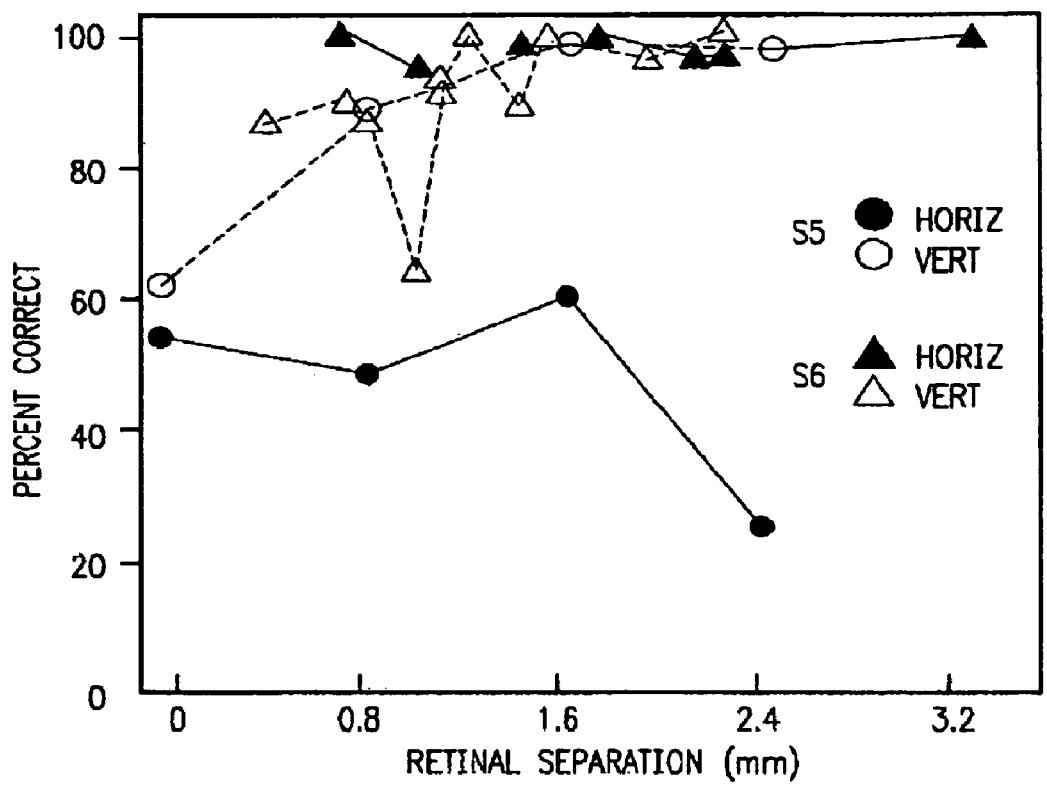
FIG. 61 shows a relative position performance.

Performance for adjacent electrodes 0.8, 1.6, and 2.4 mm apart is shown for both subjects. The subjects performed significantly better than chance (50% correct) ($p<0.05$, 1-tailed t-test) for all electrode separations. A pair of pulses on two different electrodes was presented, separated by a 300 msec time interval and subjects were asked to report if the second pulse was either above/below or left/right of the first (FIG. 61). The subjects' performance was well above chance, though in the case of Subject S5, performance was at chance for left/right discriminations. FIG. 61 shows a relative position performance. Performance is shown for two subjects; and performance for horizontal (solid line) and vertical (dashed line) discriminations are shown separately. Error bars represent binominal error estimates of the mean and are smaller that the symbols.

Figure 62:
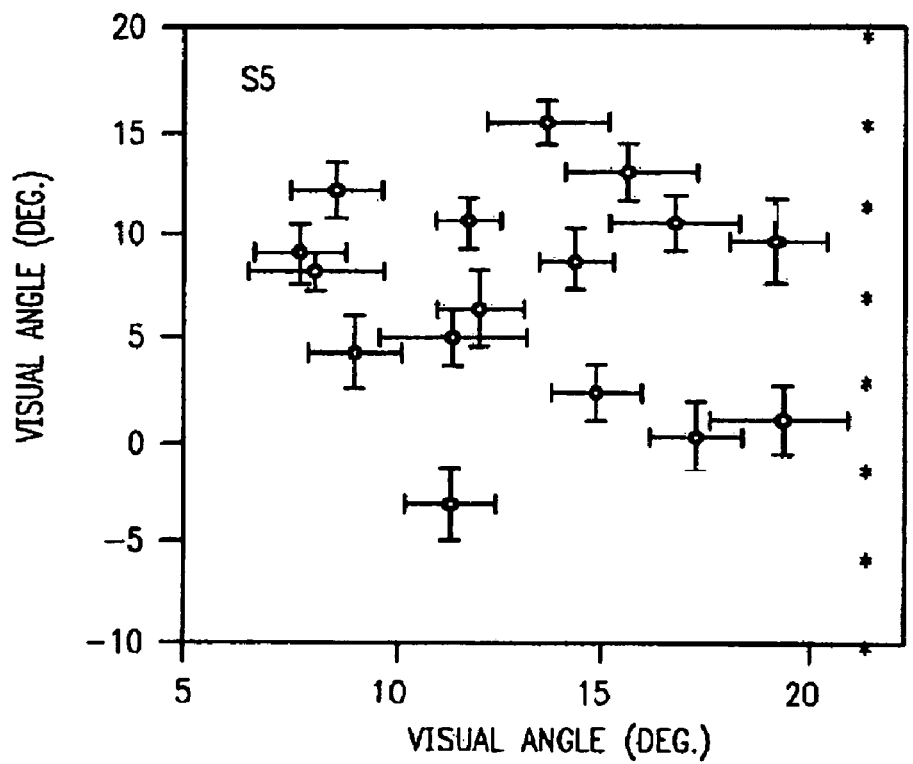
FIG. 62 shows a spatial location of phosphenes associated with individual electrodes.

A randomly chosen electrode was then stimulated with a single 0.975 ms supra-threshold pulse and the subject positioned a second magnetic token in the perceived location of the phosphene. Each electrode was stimulated twelve times. The average position of the phosphene corresponding to each electrode, relative to (0,0), was calculated. The perceived depths of the phosphenes elicited by each electrode were measured in a separate study. The results of these experiments (FIG. 62) provide evidence that each stimulated electrode consistently produces a phosphene in a specific location, and that the total visual area covered by the electrodes roughly corresponds to the physical size of the array projected into visual space. Spatial location of phosphenes associated with individual electrodes. This spatial map shows that each electrode produces a phosphene in a specific location, and that the visual angle spanned by these phosphenes is consistent with the physical size of the array.

Figure 63:
FIG. 63 shows spike thresholds for two stimulation configurations.

The spatial spread of electrical activation was measured in normal rat retina using a hexagonal multi-electrode array (FIG. 63). The recording electrode was always in the center of the array. When stimulation was at the recording electrode (left panel) threshold was 0.9 µA. When a single adjacent electrode (60 µm distant from the recording electrode) was used for stimulation (right panel), about three times more current was needed compared to stimulation at the recording electrode. This suggests that, with small electrodes (6 µm-19 µm in size), the effects of electrical stimulation tend to be narrowly focused spatially. FIG. 63 shows spike thresholds for two stimulation configurations. Filled circles indicate active electrode used for stimulation, open circles denote unused electrodes. The recording electrode (R) was always in the center. Threshold currents are shown as averages +/−SEM in 8 cells. Electrodes were 60 µm apart.

Figure 64:
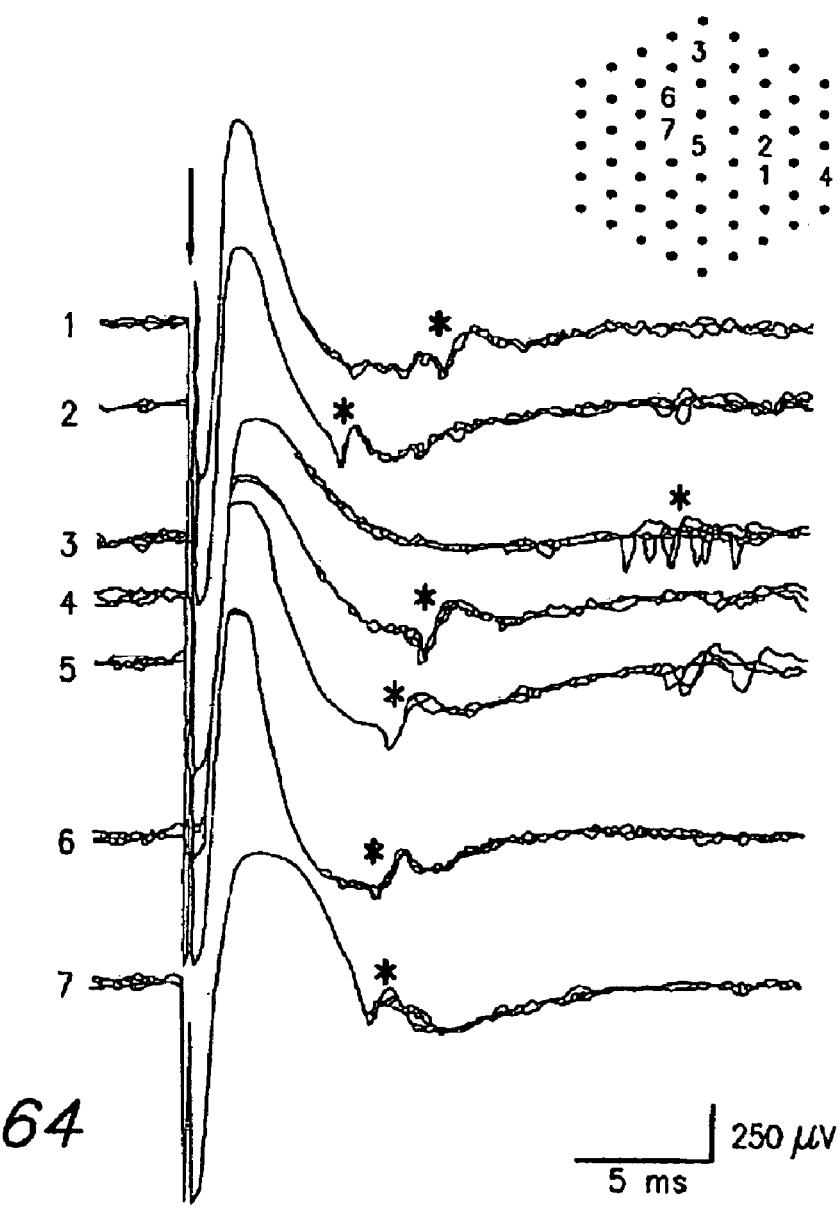
FIG. 64 shows multiple site stimulation.

The effect of stimulating seven electrodes simultaneously was examined using a multi-electrode array consisting of 10 µm electrodes separated by 60 µm. Suprathreshold pulses (0.8 µA, 0.1 msec duration) were stimulated and recorded using 7 electrodes in this array. Stimulating each electrode individually evoked spikes that could be recorded at the stimulating electrode. Then all 7 electrodes were stimulated and recorded simultaneously (FIG. 64). Simultaneous stimulation evoked seven distinct responses on the seven spatially disparate electrodes. These responses did not differ from those recorded when stimulated individually. Adjacent electrodes did not influence each other during simultaneous stimulation. Spikes recorded on one electrode were, at most, reflected as very small deflections on other electrodes. This provides further evidence (in normal retina) that 60 µm is sufficient spacing to avoid electrode interactions using small stimulating electrodes.

Figure 65:
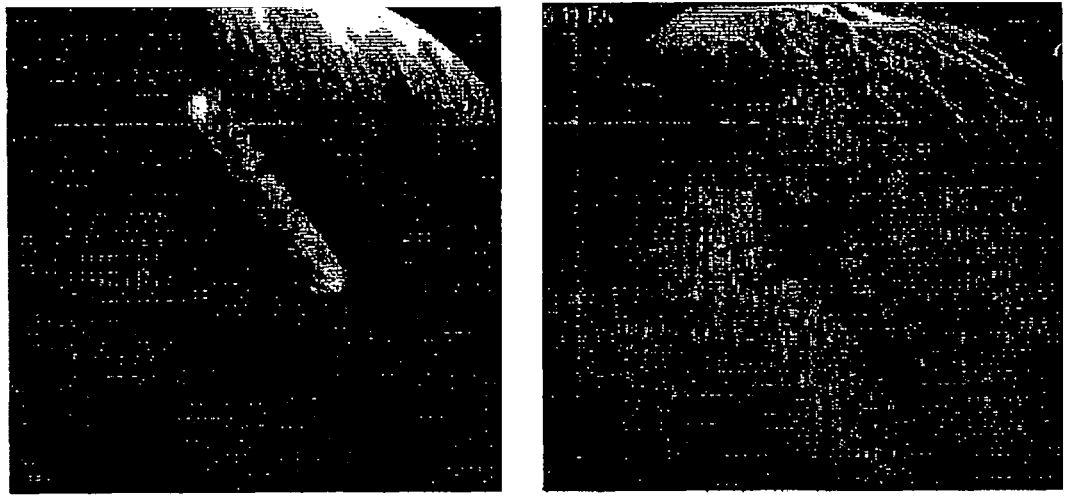
FIG. 65 shows a fundus photo and flourescein angiogram after 3 month of the preferred trans-retinal implant in a rabbit.

FIG. 65 shows a fundus photo and flourescein angiogram after 3 month of the preferred flexible circuit 1 implant in a rabbit. It is shown that the point 24 of the flexible circuit 1 cuts the retina as it is inserted. 15 rabbits were chronically implanted for over three months each with polyimide flexible circuit 1 which were from 0.3 mm to 0.7 mm, preferably about 0.5 mm wide and from 3.5 mm to 4.5 mm, preferably about 4 mm long using the preferred trans-retinal surgical approach which included laser treatment around the retinotomy site. The flexible circuit 1 were inserted under the retina and left with a portion of the flexible circuit cable 12 sticking out into the vitreous. In an actual device, according the present invention, the flex circuit cable 12 of FIG. 65 would be attached to an electronics package 14 as described above. The polyimide models were inserted under the retina and left with a portion of the model sticking out into the vitreous. It was not observed any retinal detachment, proliferate retinopathy or any other surgical complication in any of these animals over the 3-4 month implant periods (FIG. 65).

Figure 66:
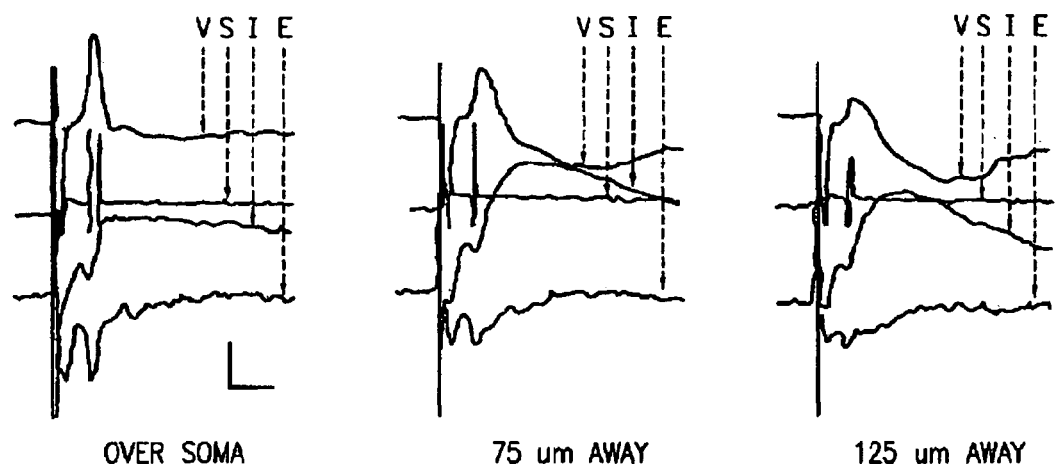
FIG. 66 shows measurements of produced by a stimulating electrode.

Longer duration pulses also stimulated ganglion cells, but in addition stimulated other cell types deeper in the retina. Patch clamp measurement of input currents to ganglion cells allowed us to directly determine if other retinal cell types are activated by electrical stimulation and affect the ganglion cell response. Excitatory input currents indicate activation of presynaptic excitatory cells (most likely bipolars) and measurement of inhibitory currents indicates activation of presynaptic inhibitory cells (most likely amacrine cells). Long duration (1 ms) pulses elicited both excitatory and inhibitory currents (FIG. 66).

Spatial spread of activation was measured by positioning the stimulating electrode at different distances from the ganglion cell soma (FIG. 65). The largest excitatory currents were elicited when the stimulating electrode was placed directly over the soma. Moving the stimulating electrode away from the soma caused a consistent decrease in the maximum amplitude of excitation (compare maximum amplitudes of excitation in the left panel vs. the middle and right panels). Surprisingly, the largest inhibitory current was generated when the stimulating electrode was not directly over the soma (FIG. 66, middle panel). Even when the stimulating electrode was 125 µm from the soma, the inhibitory current was larger than when the stimulating electrode was directly over the soma. Substantial inhibitory currents was at distances up to 225 µm from the soma. The peaks between inhibitory activity occur between and after periods of spiking. Scale bars: Vertical: 100 pA, 25 mV, Horizontal: 20 ms; applies to all panels.

The temporal duration of inhibition varied as a function of the distance between stimulating electrode and soma. Inhibition persisted longer when the stimulating electrode was 75 µm from the soma, than at 0 or 125 µm. Thus, the strength and duration of inhibition are robust at a distance of about 75 µm from the soma and decrease steadily as the distance from the soma increases beyond that. These findings suggest that long stimulus pulses generate a wave of activity that could inhibit ganglion cells' responses to subsequent pulses.

Figure 67:
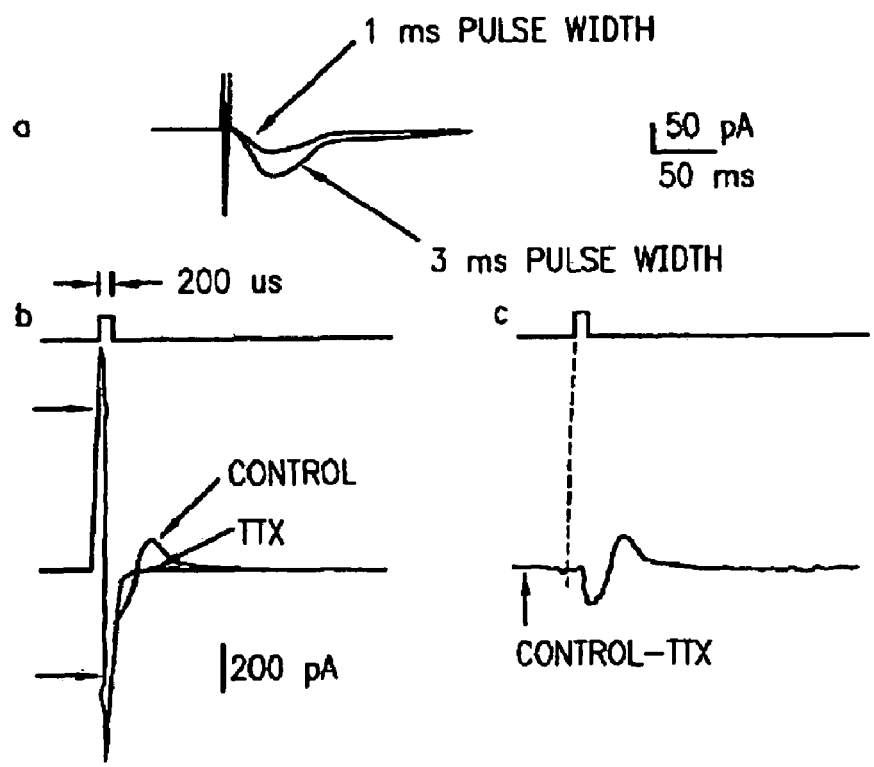
FIG. 67 shows short pulses only produce early phase spiking.

If ganglion cells could be stimulated directly without stimulating any of the excitatory or inhibitory circuitry that modifies their responses, then their responses in space and time could be accurately controlled. The observation that excitatory input elicited (via bipolar cells) by electrical stimulation function of pulse duration (longer duration pulses generate larger excitatory inputs (FIG. 67 Qa, n=2/2 cells)) suggested that decreasing the pulse duration might reduce or eliminate excitatory input to ganglion cells, and possibly reduce inhibitory input as well.

Spikes produced by short pulses were measured by subtracting out the large electrical stimulation artifact, which was isolated by applying a drug (TTX) that blocks spiking activity (FIG. 67*b*). The resulting trace (FIG. 67*c*) provides a measure of the spiking activity of the cell and short pulses only generate a single, early phase spike. This ability to generate direct ganglion cell spiking was found consistently in 16 cells. This suggests that short pulses directly stimulate ganglion cells and avoid modification of their response by excitatory or inhibitory inputs.

Figure 68:
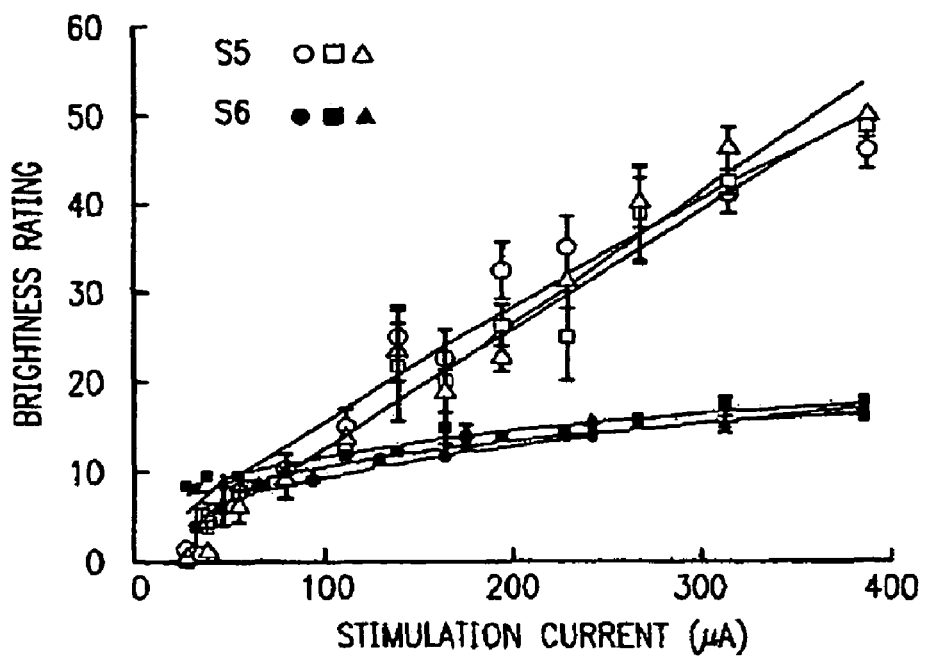
FIG. 68 shows brightness rating as a function of stimulation current for two observers.

FIG. 68 shows example curves showing brightness ratings as a function of stimulation intensity for S5 and S6. Brightness ratings were measured by presenting each subject with an easily visible "standard pulse" (rated by default as a "10") and having the subject rate subsequently presented pulses that varied in amplitude "20" if they were twice as bright as the standard pulse, "5" if they were half as bright as the standard pulse, and so on. The standard pulse was presented in between each trial. In the case of normal vision, apparent brightness increases monotonically but compressively with luminance. It seems that apparent brightness also increases monotonically but slightly compressively with stimulation amplitude.

Although the brightness rating ranges of these two subjects differ, they can both identify different brightness levels with similar accuracy. The number of brightness steps that subjects can identify can be calculated from the standard deviation of their brightness ratings (standard errors are shown in FIG. 68). These calculations suggest that Subject 5 can identify 6 brightness levels and Subject 6 can identify 6.5 brightness levels with 95% accuracy.

Figure 69:
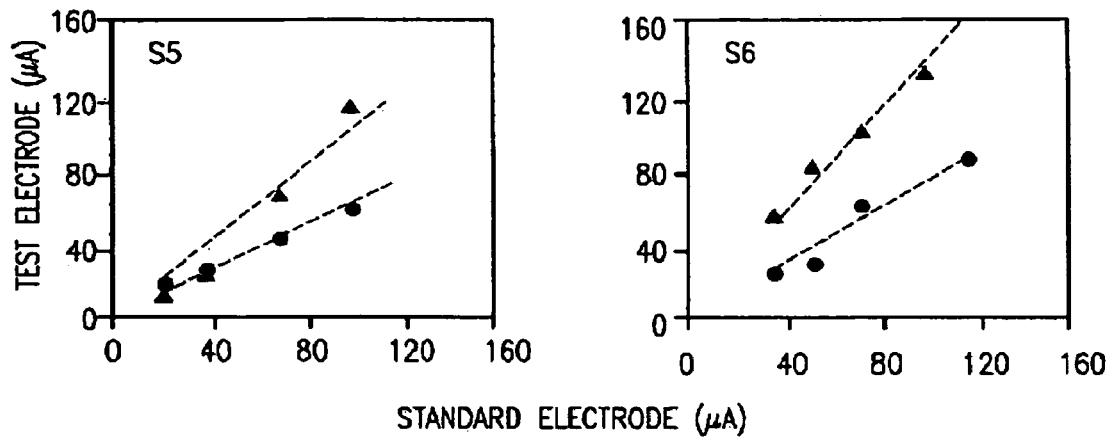
FIG. 69 shows short electrical pulses.

The brightness functions of different electrodes using a two interval brightness matching technique were compared. In one of the two intervals subjects were presented with a pulse on one electrode at a standard current intensity. In the second of the two intervals (these two intervals were presented in a random order) subjects were presented with a pulse on a different test electrode. Subjects judged which of the pulses were brighter and the current intensity on the test electrode was varied to find the value where standard and test pulses appeared equally bright. This procedure was repeated for a range of current levels on the standard electrode. FIG. 69 plots the test electrode current required to match the 'standard' electrode for 2 electrodes in two subjects. The x-axis represents the current intensity on the standard electrode and the y-axis represents current intensity on two test electrodes. A linear fit with zero intercept (shown with dashed lines) describes the data well. These functions will allow us to match brightness across electrodes so that objects will not change in their apparent brightness as they move to a different position on the electrode array. It is also possible to indirectly measure the number of brightness steps that subjects can discriminate from these data based on the slopes of the brightness matching function. These calculations suggest that subjects can discriminate 6 brightness levels with 95% accuracy, similar to the estimate from brightness rating measurements.

Figure 70:
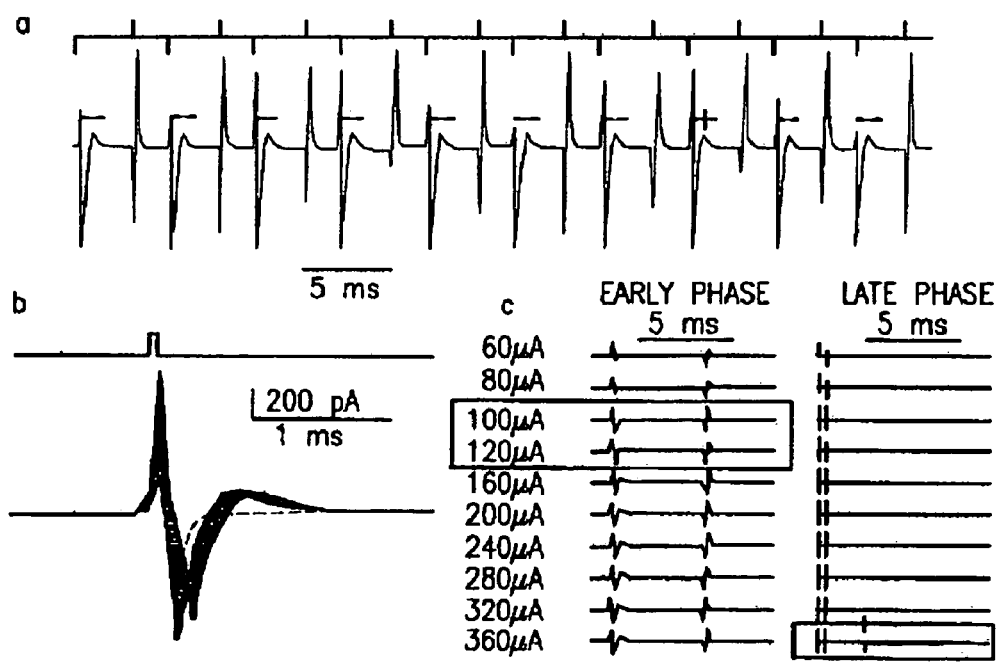
FIG. 70 shows the effect of burst frequency.

Short duration stimulus pulses elicited a single spike per pulse (asterisks); spikes were phase locked to the stimulus (FIG. 70*a*, top). Similar responses were observed in 12 cells at all frequencies tested (>250 Hz; ganglion cells can generate light elicited spiking at rates up to 250 Hz). This is demonstrated in FIG. 70*b*. The time interval from 1 ms before to 2 ms was extracted after each cathodic pulse and overlaid these traces. These individual traces were extremely consistent. Comparison of these overlaid responses with responses using TTX (which blocks spiking activity; dotted trace) indicates that each pulse elicits a single spike with a very consistent phase lag.

It was possible to consistently generate one spike per pulse over a wide range of stimulus amplitudes, as shown in FIG. 70*c*. The two columns represent two different time scales. The left column indicates that at above threshold levels, stimulus pulses elicited spikes, as shown by the small deflection in the stimulus artifact trace (vertical arrow, left gray box). The threshold at which spiking occurred was determined by comparing the shape of the early phase response to the shape of the response when spiking activity was blocked by TTX (FIG. 70*b*). This early phase response persisted for all stimulus levels above threshold. For this cell the threshold was around 100-120 µA. For the population (n=13), the mean threshold amplitude was 193±64 µA.

At higher amplitude levels, late phase spiking was elicited (FIG. 70*c* right column, right gray box). For this cell late phase spiking was observable at stimulus amplitudes above 340 µA. Thus, late phase spikes were not observed until stimulation levels were almost 2.8× threshold amplitude.

Because short pulses enable us to elicit spikes in ganglion cells with such exquisite reliability, it is possible to mimic responses to light stimuli with surprising accuracy. The spiking response was measured to the flash of a small square of light and then constructed a series of electrical pulses that mimicked the light evoked spiking pattern. This electrical pulse pattern produced a pattern of elicited spikes whose temporal pattern precisely matched the pattern of light-elicited spikes. Jitter between individual light- and pulse-elicited spikes was less than 0.5 ms. Different spike patterns (such as responses to changes in light luminance levels) could also be replicated. These data were collected in normal rabbit retina. The short pulses can generate single ganglion cell spikes up to very high frequencies with multi-electrode recordings in degenerated rat retina. Rapid pulse pairs (200 Hz interval) evoked spikes with 99% reliability (71 spikes out of 72 pulse pairs; 3 ganglion cells). In another experiment, biphasic pulses were presented at 50 Hz for several seconds. Single spikes were generated throughout the stimulation period with 94% reliability (656 spikes out of 689 pulses; 3 cells). These results confirm that short electrical pulses can be used to precisely control the spiking pattern of ganglion cells in degenerated retina.

Figure 71:
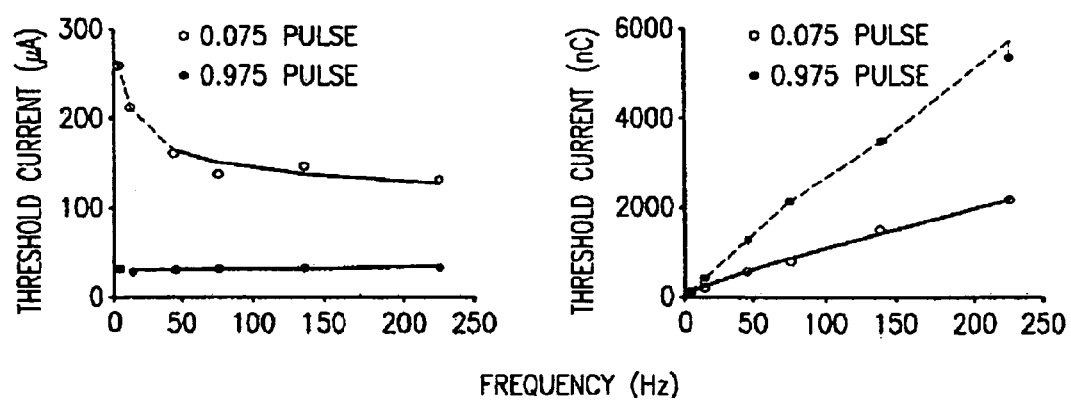
FIG. 71 shows the current required to reach threshold for a 200 ms interval of pulses.

The pulse frequency can be used to manipulate brightness in human subjects. The first panel of FIG. 71 shows the current required to reach threshold for a 200 ms interval of pulses as a function of frequency of pulses in the interval. This typical example is from Subject 6. The second panel re-plots these data to show the charge required to reach threshold. The current needed to reach threshold decreases as a function of pulse frequency; however the charge needed to reach threshold increases as a function of frequency.

As shown by the solid lines in FIG. 71 the data describing brightness as a function of frequency can be fit by the equations $J=eP^g$ and $C=epP^g$ where I is the current needed to reach threshold, C is the charge needed to reach threshold, p is the pulse width, and e and g are experimentally determined. Brightness was also measured as a function of frequency using a supra threshold brightness matching procedure. Suprathreshold curves followed a similar function as the threshold curves.

For a 200 msec pulse train the drop in the amount of current needed as a function of frequency begins to asymptote at higher frequency levels. However, data with shorter pulse train intervals (not shown) suggests that this may be due to rapid adaptation effects, and for shorter bursts, rate coding may be possible using even very high frequencies. These data suggest that it is possible to use frequency to manipulate the brightness of percepts. However, this will come at a cost as far as charge efficiency is concerned. The decrease in charge efficiency as a function of frequency is less severe for short (0.075) pulses than for long (0.975) pulses (data not shown) suggesting that a frequency coding approach to coding brightness in human subjects will most likely require the use of short pulses.

The invention relates to an implantable device to affect an eye, the eye having a retina, a sclera, and a vitreous cavity, said device comprising:
 a retinal implant that is positioned subretinally;
 said retinal implant comprising at least one electrode connected with a stimulating source;
 at least one connection with said stimulating source and with said at least one electrode, wherein said connection is suitable to pass transretinally into the vitreous cavity of the eye;
 said connection suitably designed to pass through the sclera at a point where there is no retina; and
 said stimulating source is suitable to be located outside the sclera.

The retinal implant is configured to enable electrical stimulation of a retina of an eye to produce artificial vision.

The stimulating source is comprised of a source of electrical signal. The connection is comprised of an electrical lead. At least one electrode that is configured to pass an electrical signal to the retina. The retinal implant that is positioned subretinally is suitable to be positioned between the photoreceptor cell layer and the retinal pigment epithelium. The stimulating source comprises electrical coupling with a secondary coil, which receives electromagnetic signals from a primary coil, said primary coil located outside the sclera. The secondary coil is suitable to be located inside the eye. The secondary coil is suitable to be located outside the sclera.

The invention relates to an implantable device to deliver drugs to an eye, the eye having a retina, a sclera, and a vitreous cavity, said device comprising:
 a retinal implant that is positioned subretinally for drug release;
 said retinal implant comprising a drug delivery device connected with a drug reservoir;
 at least one connection between said drug reservoir and said retinal implant, wherein said connection is suitable to pass transretinally into the vitreous cavity of the eye;
 said connection being suitable to pass through the sclera at a point where there is no retina; and
 said drug reservoir is located outside the eye.

The implantable device delivers the drugs electrophoretically. The connection comprises a tube. The retina additionally is comprised of a photoreceptor cell layer and a retinal pigment epithelium wherein said retinal implant that is positioned subretinally is suitable to be positioned between the photoreceptor cell layer and the retinal pigment epithelium.

The invention relates to an artificial retinal device to electrically stimulate a retina of an eye to produce artificial vision, the eye having a sclera, and a vitreous cavity, said artificial retinal device comprising:
 a retinal implant that is positioned subretinally;
 said retinal implant comprising at least one stimulating electrode connected with an electrical source that is located outside the eye;
 at least one electrical lead connected with said electrical source and with said at least one stimulating electrode, wherein said electrical lead is suitable to pass transretinally into the vitreous cavity of the eye; and
 said electrical lead passing through the sclera at a point where there is no retina.

The electrical source is suitable to affix to the sclera of the eye with sutures. The electrodes are facing the retinal. The retina additionally is comprised of a photoreceptor cell layer and a retinal pigment epithelium wherein said retinal implant that is positioned subretinally is suitable to be positioned between the photoreceptor cell layer and the retinal pigment epithelium.

The invention relates to an implantable device drug delivery device to deliver drugs for treatment to affect an eye, the eye having a retina, a sclera, and a vitreous cavity, said device comprising:
 a retinal implant that is positioned subretinally;
 said retinal implant comprising at least one orifice connected with a drug reservoir;
 at least one delivery conduit connected with said drug reservoir and with said at least one orifice, wherein said delivery conduit is suitable to pass transretinally into the vitreous cavity of the eye;
 said delivery conduit suitably designed to pass through the sclera at a point where there is no retina; and
 said drug reservoir is suitable to be located outside the sclera.

The implant releases said drugs electrophoretically. The delivery conduit is a tube that transfers said drugs from said drug reservoir to said retinal implant. The drug is suitable to stimulate living tissue. The retinal implant that is positioned subretinally is suitable to be positioned between the photoreceptor cell layer and the retina pigment epithelium. The implantable device comprises an electrophoretic drug delivery device. The retinal implant is configured to enable drug stimulation of a retina of an eye to produce artificial vision.

The invention relates to a method for producing an artificial retinal device suitable to electrically stimulate a retina of an eye to produce artificial vision, the eye having a sclera, and a vitreous cavity, said method comprising the steps of:
 selecting a biocompatible retinal implant;
 placing at least one stimulating electrode in said retinal implant that is suitable for electrically stimulating the retina;
 connecting an electrical lead to said stimulating electrode;
 adapting said electrical lead to pass transretinally into the vitreous cavity of the eye;
 attaching said electrical lead to an electrical source that is located outside the eye; and
 passing said electrical lead through the sclera at a point where there is no retina.

The invention relates to a method for producing artificial vision in an eye using an artificial retinal device, the eye having a sclera, a retina, and a vitreous cavity, wherein said artificial retinal device comprises a retinal implant further comprising at least one stimulating electrode in said retinal implant, said stimulating electrode connected with an electrical source, at least one electrical lead connected with said electrical source and said electrode, the method comprising the steps of:
 adapting said retinal implant to be positionable in the subretinal position in the eye;
 adapting said electrical lead to be suitable to pass transretinally through the retina of the eye into the vitreous cavity; and
 adapting said electrical lead to be suitable to pass through the sclera at a point where there is no retina.

The method comprises the step of attaching said electrical source to the sclera by sutures.

The method further comprises the step of positioning said electrodes to face the retina.

The invention relates to a visual prosthesis, comprising:

means for perceiving a visual image where said means is suitable to be located outside the eye of a user, said means producing a visual signal output in response thereto;

retinal tissue stimulation means adapted to be operatively attached to a retina of a user, where said retinal stimulation means is suitable to be located below the retina of a user; and wireless visual signal communication means for transmitting said visual signal output to said retinal tissue stimulation means.

The invention relates to a method of at least partially restoring vision to a user who suffers from photoreceptor degenerative retinal conditions of the eye, comprising the steps of:

perceiving a visual image and producing a visual signal output in response thereto;

wirelessly transmitting the visual signal output into the eye of a user; and stimulating retinal tissue of the user by means of an electrode, that is suitable to be placed below the retina of a user, in accordance with the visual signal output.

The invention relates to a flexible circuit electrode array comprising:

a polymer base layer;

metal traces deposited on said polymer base layer, including electrodes suitable to stimulate neural tissue; and said polymer base layer and said metal traces are embedded in a body having a generally oval shape in the plane of the retina, said oval shaped body being curved such that it substantially conforms to the spherical curvature of the retina of the recipient's eye.

The flexible circuit electrode array comprises at least one mounting aperture in said body for attaching the electrode array to the retina with a tack. The oval shaped body has a radius of spherical curvature, which is smaller than the radius of the curvature of the eye. The oval shaped body is made of a soft polymer containing silicone having hardness of about 50 or less on the Shore A scale as measured with a durometer. The flexible circuit cable portion has an angle of about 45° to about 180°. The flexible circuit cable portion has a bend with an angle of about 60° to about 120°. The flexible circuit cable portion has a bend with an angle of about 45° to about 180°. The flexible circuit cable portion has a bend with an angle of about 60° to about 120°. The flexible circuit cable portion has a fold within the attached flexible circuit electrode array with an angle of about 1° to about 180°. The flexible circuit cable portion has a fold within the attached flexible circuit electrode array with an angle of about 20° to about 90°. The flexible circuit cable portion has a horizontal angle within the attached flexible circuit electrode array of about 1° to about 90°. The flexible circuit cable portion has a horizontal angle within the attached flexible circuit electrode array of about 10° to about 45°. The flexible circuit cable portion comprises at least one grooved or rippled pad for capturing a mattress suture. The flexible circuit electrode array is positioned on the surface of the body having a generally oval shape. The soft insulating material is positioned on the surface between said electrodes. The film containing a soft polymer is applied on said flexible circuit cable portion. The film containing a soft polymer contains silicone. The film containing a soft polymer comprises a ladder like structure. The film containing a soft polymer contains beads and/or bumpers.

The invention relates to a method of making a flexible circuit electrode array comprising:

depositing a polymer base layer;

depositing metal on said polymer base layer;

patterning said metal to form metal traces;

depositing a polymer top layer on said polymer base layer and said metal traces; and heating said flexible circuit electrode array in a mold to form a three dimensional shape in said flexible circuit electrode array.

The method further comprising the steps of heating said flexible circuit electrode array in successively smaller molds. The step of depositing said polymer base layer and said polymer top layer is depositing polyimide. The step of depositing said polymer base layer and said polymer top layer is depositing silicone. The step of depositing said polymer base layer and said polymer top layer is depositing fluoro-polymer. The method further comprising forming a twist in a flexible circuit cable portion of said flexible circuit electrode array.

Accordingly, what has been shown is improved methods of making a neural electrode array and improved methods of stimulating neural tissue. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What we claim is:

1. A flexible circuit comprising:

a polymer base layer;

metal traces deposited on said polymer base layer, including electrodes suitable to stimulate neural tissue;

a polymer top layer deposited on said polymer base layer and said metal traces, forming an electrode array portion and a cable portion;

a body having a generally convex oval shape in the plane of the retina, said oval shaped body being curved such that it substantially conforms to the spherical curvature of the retina of the recipient's eye, said array portion embedded in said body, and said metal traces are electrically coupled by said cable portion to an electronics package that generates stimulation signals, wherein said cable portion is adapted to pierce a sclera of the recipient's eye and the electronics package is adapted to be external to the sclera.

2. The flexible circuit according to claim 1 comprising 1 to 1000 electrodes.

3. The flexible circuit according to claim 2 comprising 16 to 250 electrodes.

4. The flexible circuit according to claim 3 comprising 60 to 250 electrodes.

5. The flexible circuit according to claim 1 wherein the flexible circuit is from 0.3 mm to 0.7 mm wide.

6. The flexible circuit according to claim 1 wherein the flexible circuit is from 3.5 mm to 4.5 mm long.

7. The flexible circuit according to claim 1 wherein the spacing between the electrodes is 5 μm-500 μm.

8. The flexible circuit according to claim 7 wherein the spacing between the electrodes is 250 μm-500 μm.

9. The flexible circuit according to claim 8 wherein the spacing between the electrodes is 50 μm-500 μm.

10. The flexible circuit according to claim 1 wherein the electronic package has 200 to 300 channels.

11. The flexible circuit according to claim 1 wherein the electronic package has 240 to 260 channels.

12. The flexible circuit electrode array of claim 1, wherein the body comprises polymer material embedding the flexible circuit electrode array.

13. The flexible circuit electrode array of claim 1, wherein the body comprises pliable material along edges of the polymer base layer.

14. The flexible circuit electrode array of claim 1, wherein the body comprises an attachment point on the polymer base layer, and wherein the attachment is adapted for holding a retinal tack and the retinal tack is adapted to hold the electrode array to the retina.

15. The flexible circuit of claim 1, further comprising pliable material along a length of the cable, and wherein the pliable material holds the electrode array away from retinal tissue.

16. The flexible circuit of claim 1, further comprising a service loop in the cable portion to allow lifting of the electrode array off the retina without harming the retina.

17. The flexible circuit of claim 1, further comprising a fold in said cable to reduce tension and enable effective attachment of the flexible circuit electrode array to the retina.

18. The flexible circuit electrode array of claim 1, wherein the electrode array is coupled to a drug reservoir, wherein drugs are delivered from the drug reservoir to the retina based on the stimulation signals to the flexible circuit electrode array.

* * * * *